(12) United States Patent
Suginouchi et al.

(10) Patent No.: US 7,046,015 B2
(45) Date of Patent: May 16, 2006

(54) ULTRASONIC DISTANCE MEASURE

(75) Inventors: Takehiko Suginouchi, Soraku-gun (JP); Koichi Saito, Yokohama (JP); Masahiko Hashimoto, Shijonawate (JP)

(73) Assignee: Matsushita Electric Industrial Co., Ltd., Kadoma (JP)

( * ) Notice: Subject to any disclaimer, the term of this patent is extended or adjusted under 35 U.S.C. 154(b) by 0 days.

(21) Appl. No.: 11/214,426

(22) Filed: Aug. 29, 2005

(65) Prior Publication Data

US 2006/0022680 A1    Feb. 2, 2006

Related U.S. Application Data

(63) Continuation of application No. PCT/JP2005/007915, filed on Apr. 26, 2005.

(30) Foreign Application Priority Data

Apr. 28, 2003   (JP) ............................... 2004-133303

(51) Int. Cl.
   *G01R 27/32*   (2006.01)

(52) U.S. Cl. ........................................ 324/635; 73/609

(58) Field of Classification Search ..................... None
   See application file for complete search history.

(56) References Cited

U.S. PATENT DOCUMENTS 3,914,987 A * 10/1975 Bickel et al. ................. 73/609
6,323,441 B1 * 11/2001 Hager et al. ..................... 177/1

FOREIGN PATENT DOCUMENTS

| JP | 58-005099 | 1/1983 |
| JP | 61-220593 | 9/1986 |
| JP | 63-009876 | 1/1988 |
| JP | 07-104063 | 4/1995 |
| JP | 52-088013 | 7/1997 |

* cited by examiner

*Primary Examiner*—Vincent Q. Nguyen
(74) *Attorney, Agent, or Firm*—Renner, Otto, Boisselle & Sklar, LLP

(57) ABSTRACT

An ultrasonic distance measure includes: transmitting and receiving ultrasonic transducers with changeable resonant/resonance frequencies; a driving section generating a frequency-modulated drive signal to drive the transducer and transmit an ultrasonic wave; a transmitting control voltage generating section for generating a control voltage to change the resonant/resonance frequency of The transducer and applying it to the transducer in transmitting the ultrasonic wave; a receiving control voltage generating section for generating a control voltage to change the resonant/resonance frequency of the transducer and applying it to the transducer when a controllable amount of time delay has passed since The drive signal was generated; and a receiving section for sensing the intensity of a signal received as the ultrasonic wave at the transducer.

20 Claims, 22 Drawing Sheets

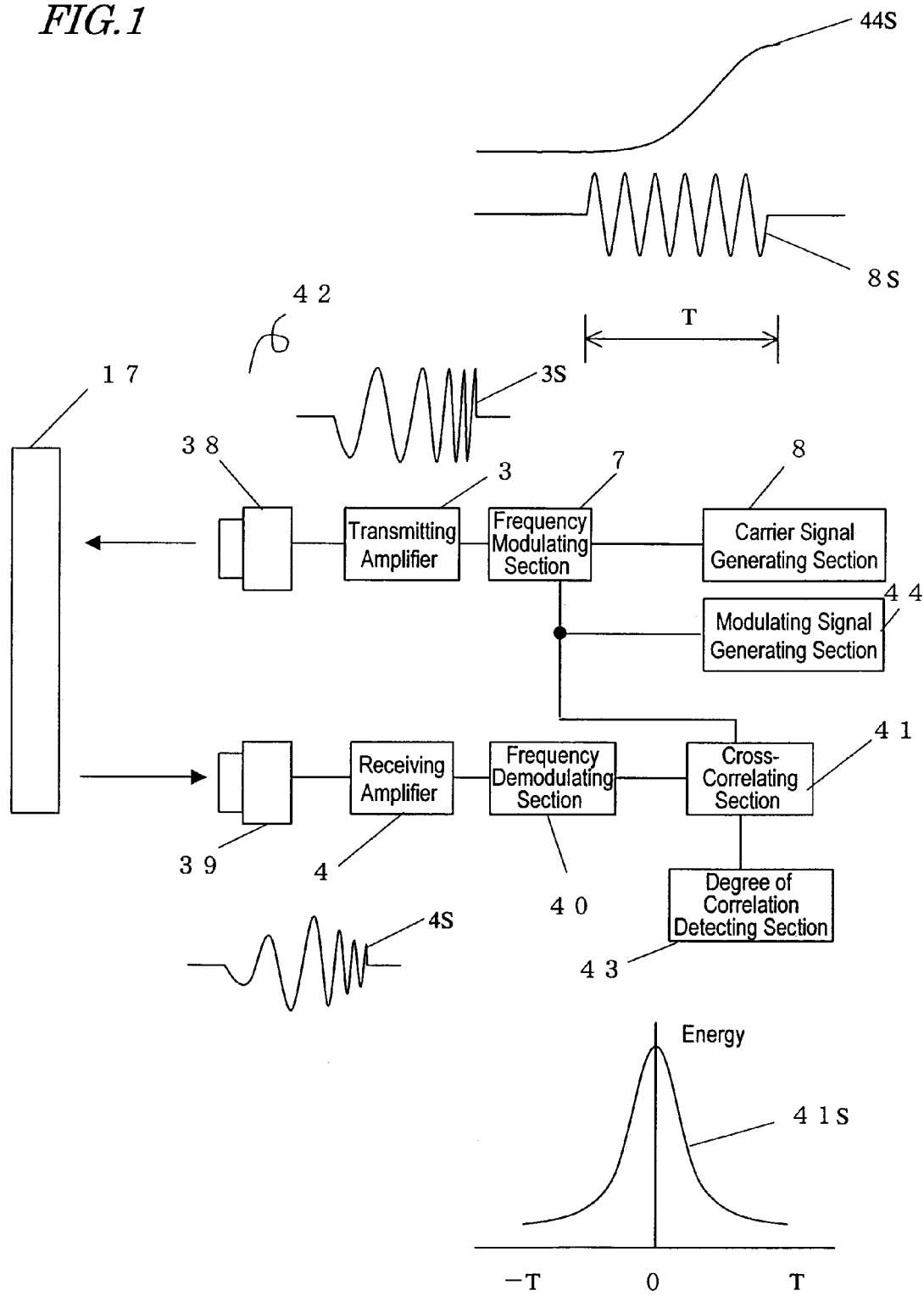

ULTRASONIC DISTANCE MEASURE

This is a continuation of International Application PCT/JP2005/007915, with an international filing date of Apr. 26, 2005.

BACKGROUND OF THE INVENTION

1. Field of the Invention

The present invention relates to an ultrasonic distance measure for estimating the distance to an object by measuring the propagation time of an ultrasonic wave. The present invention also relates to an ultrasonic transducer for use in the ultrasonic distance measure.

2. Description of the Related Art

An ultrasonic distance measure transmits an ultrasonic wave toward an object and receives the ultrasonic wave that has been reflected from the object, thereby measuring the propagation time of the ultrasonic wave and calculating the distance to the object based on the propagation time. An ultrasonic wave propagates through a gas or a liquid. That is why if the velocity at which the ultrasonic wave is propagating through the medium is known, then the distance to the object in the air or in the liquid can be calculated.

According to this principle of measurement, it is important for an ultrasonic distance measure to accurately define when a wave reflected from an object returned to the distance measure. In general, when the intensity of the reflected wave received reaches a predetermined sensing level, the ultrasonic distance measure acknowledges the sensing of the reflected wave and defines the time when the reflected wave arrived.

The ultrasonic wave attenuates while propagating through the medium, and therefore, the intensity of the reflected wave received changes according to the distance to the object. That is why according to a known technique, to sense a reflected wave accurately, a plurality of sensing levels are set for respective distances to measure such that a relatively high sensing level is adopted to measure a short distance and that a relatively low sensing level is adopted to measure a long distance. On the other hand, according to another known technique, the rise of a reflected wave received is accurately sensed by setting a plurality of sensing levels at a time. According to yet another technique, the waveform of an ultrasonic wave to transmit is given a special mark by inverting its phase, for example, and the arrival of its reflected wave is sensed by detecting that mark.

Also, in measuring with an ultrasonic distance measure, the accuracy of measurement is affected by fluctuation of the medium or surrounding noise. To avoid such an influence, Japanese Patent Application Laid-Open Publication No. 7-104063 discloses an ultrasonic distance measure for measuring the propagation time of an ultrasonic wave by subjecting an ultrasonic wave to transmit to frequency modulation and a signal representing a reflected wave received to correlation processing, respectively. As shown in FIG. 1, in such an ultrasonic distance measure, a carrier signal generating section 8 generates a carrier signal 8S as a burst wave and a modulating signal generating section 44 generates a modulating signal 44S for changing the frequency of the burst wave from f0 to f1 within a period T. A frequency modulating section 7 modulates the frequency of the carrier signal 8S with the modulating signal 44S and then outputs the resultant signal to a transmitting amplifier 3. In response to a signal from the modulating signal generating section 44, the transmitting amplifier 3 outputs a drive signal 3S to a transmitting ultrasonic transducer 38.

The ultrasonic wave, transmitted by the transmitting ultrasonic transducer 38 in response to the drive signal 3S, is reflected from an object 17. And the reflected wave reaches a receiving ultrasonic transducer 39. A received signal, representing the reflected wave received at the receiving ultrasonic transducer 39, is amplified by a receiving amplifier 4 to be a received signal 4S. Then, a frequency demodulating section 40 demodulates the received signal 4S.

Next, a cross-correlating section 41 sequentially causes a delay in the modulating signal 44S at regular time intervals since the time when that signal was generated, and obtains a cross-correlation function 41S representing a correlation between the delayed signal and the demodulated received wave. A degree of correlation detecting section 43 detects a time delay with the highest degree of correlation as a propagation time in the cross-correlation function 41S.

The apparatus disclosed in Patent Document No. 1 uses a frequency-modulated ultrasonic wave, and its ultrasonic transducers need to operate in a relatively wide frequency range. However, an ultrasonic transducer generally used produces an ultrasonic wave by utilizing the resonance phenomenon of a piezoelectric ceramic. Thus, according to its operating principle, such an ultrasonic transducer can produce an ultrasonic wave only within a narrow range in the vicinity of its resonant frequency. Accordingly, if the frequency of an ultrasonic wave should be modulated in a range that is broad enough to avoid the effects of noise sufficiently, then it would be difficult to drive the ultrasonic transducers all through that broad range.

Some ultrasonic transducers can operate in a wide frequency range. However, such ultrasonic transducers need to be driven with a high output and are hard to drive with a battery, for example. Also, if the frequency range broadens, then the ultrasonic transducer on the receiving end is likely to collect noise, which is a problem.

SUMMARY OF THE INVENTION

In order to overcome the problems described above, an object of the present invention is to provide an ultrasonic distance measure that realizes high-accuracy measurements with a simple configuration.

An ultrasonic distance measure according to the present invention includes: a transmitting ultrasonic transducer and a receiving ultrasonic transducer, of which the resonant or resonance frequencies are changeable; a driving section, which generates a frequency-modulated drive signal to drive the transmitting ultrasonic transducer and transmit an ultrasonic wave; a transmitting control voltage generating section for generating a control voltage to change the resonant or resonance frequency of the transmitting ultrasonic transducer and applying the control voltage to the transmitting ultrasonic transducer that is going to transmit the ultrasonic wave; a receiving control voltage generating section for generating a control voltage to change the resonant or resonance frequency of the receiving ultrasonic transducer and applying the control voltage to the receiving ultrasonic transducer when a controllable amount of time delay has passed since the drive signal was generated; and a receiving section for sensing the intensity of a signal received as the ultrasonic wave at the receiving ultrasonic transducer. The ultrasonic wave is transmitted from the transmitting ultrasonic transducer toward an object of measurement a number of times, reflected, and then received at the receiving ultrasonic transducer with the time delay changed every time. The ultrasonic distance measure calculates propagation time of the ultrasonic wave based on the time delay that makes the receiving section receive the ultrasonic wave as a signal with the highest intensity, and measures a distance to the object of measurement based on the propagation time.

In one preferred embodiment, the ultrasonic distance measure further includes a timing section for generating and outputting a trigger signal that activates the driving section, the transmitting control voltage generating section and the receiving control voltage generating section at predetermined timings, and the receiving control voltage generating section includes a delay section for producing time delays of different lengths at regular time intervals every time the delay section receives the trigger signal.

In another preferred embodiment, the ultrasonic distance measure further includes a propagation time premeasuring section, which receives the trigger signal from the timing section and measures how much time has passed after the trigger signal was received and before the signal received at the receiving ultrasonic transducer reaches a predetermined level. The receiving control voltage generating section produces the time delays based on the amount of time measured by the premeasuring section and responsive to the trigger signal supplied from the timing section.

In another preferred embodiment, the receiving control voltage generating section and the transmitting control voltage generating section generate control voltages that change the resonant or resonance frequencies of the receiving and transmitting ultrasonic transducers substantially in sync with the frequency modulation of the drive signal.

Another ultrasonic distance measure according to the present invention includes: a transmitting ultrasonic transducer and a receiving ultrasonic transducer, of which the resonant or resonance frequencies are changeable; a driving section, which generates a measuring drive signal to drive the transmitting ultrasonic transducer and transmit a measuring ultrasonic wave, the measuring; drive signal including a first drive signal that is frequency-modulated and generated a number of times at a predetermined time interval; a transmitting control voltage generating section for generating a first control voltage to change the resonant or resonance frequency of the transmitting ultrasonic transducer and applying the control voltage to the transmitting ultrasonic transducer that is going to transmit the ultrasonic wave; a receiving control voltage generating section for generating the first control voltage to change the resonant or resonance frequency of the receiving ultrasonic transducer and applying the first control voltage to the receiving ultrasonic transducer when a predetermined time delay has passed since the first drive signal was generated each time; and a receiving section for sensing the intensity of a signal received as the ultrasonic wave at the receiving ultrasonic transducer. The ultrasonic wave is transmitted from the transmitting ultrasonic transducer toward an object of measurement a number of times in response to the first drive signal with one of the time interval and time delay fixed and the other changed, reflected as a first reflected wave each time, and then received at the receiving ultrasonic transducer. The ultrasonic distance measure calculates propagation time of a first ultrasonic wave based on the intensity of a first received signal detected at the receiving section each time and measures a distance to the object of measurement based on the propagation time.

In one preferred embodiment, the time interval is fixed and the time delay is changed.

In an alternative preferred embodiment, the time delay is fixed and the time interval is changed.

In another preferred embodiment, the receiving section locates the barycenter of the intensity of the first received signal on the axis of time delay and derives the propagating time of the first ultrasonic wave with respect to the barycenter.

In another preferred embodiment, the receiving control voltage generating section and the transmitting control voltage generating section generate the first control voltage that changes the resonant or resonance frequencies of the receiving and transmitting ultrasonic transducers substantially in sync with the frequency modulation of the first drive signal.

In another preferred embodiment, the driving section generates a second drive signal, which switches a first frequency into a second frequency, such that the measuring drive signal includes the second drive signal before the first drive signal. The receiving control voltage generating section generates a second control voltage, which produces resonance in the receiving ultrasonic transducer at the first frequency, before the first control voltage. The receiving ultrasonic transducer receives a second reflected wave resulting from a second ultrasonic wave that has been transmitted from the transmitting ultrasonic transducer toward the object of measurement in response to the second drive signal. And the receiving section detects a variation in the intensity of a second received signal representing the second reflected wave, and sets the time delay based on results of detection.

In another preferred embodiment, the drive signal is a chirp signal.

In an alternative preferred embodiment, the drive signal is a pulse signal.

In another preferred embodiment, the ultrasonic distance measure further includes a thermometer for measuring an environmental temperature around the object of measurement, and corrects propagation velocity of the ultrasonic wave according to the environmental temperature measured and calculates the distance to the object of measurement based on the propagation velocity corrected.

In another preferred embodiment, each of the transmitting and receiving ultrasonic transducers includes a diaphragm, a piezoelectric transducer provided for the diaphragm, and an actuator for shrinking or stretching the diaphragm in response to either the control voltage or the first control voltage.

In an alternative preferred embodiment, each of the transmitting and receiving ultrasonic transducers includes a resonator, a piezoelectric transducer provided for the resonator, and an actuator for changing the resonance frequency of the resonator in response to either the control voltage or the first control voltage.

In another alternative preferred embodiment, each of the transmitting and receiving ultrasonic transducers includes a first acoustic matching layer, a piezoelectric transducer, a second acoustic matching layer provided between the first acoustic matching layer and the piezoelectric transducer, and an actuator for increasing or decreasing the thickness of the second acoustic matching layer in response to either the control voltage or the first control voltage.

In a specific preferred embodiment, the second acoustic matching layer is a liquid.

A direction finder according to the present invention includes a plurality of ultrasonic distance measures according to any of the preferred embodiments of the present invention described above and finding the direction of the object of measurement based on the distances to the object of measurement as measured by the ultrasonic distance measures.

A flowmeter according to the present invention includes the ultrasonic distance measure according to any of the preferred embodiments of the present invention described above. The transmitting and receiving ultrasonic transducers of the ultrasonic distance measure are arranged so as to face each other with the channel of a fluid interposed and the flowmeter calculates the flow velocity and flow rate of the fluid based on the propagation time of the ultrasonic wave.

An ultrasonic range finding method according to the present invention includes the steps of: transmitting an ultrasonic wave toward an object of measurement by driving a transmitting ultrasonic transducer with a frequency-modulated drive signal applied thereto and with its resonant or resonance frequency changed substantially in sync with the frequency modulation of the drive signal; and receiving the ultrasonic wave, which has been reflected from the object of measurement, at the receiving ultrasonic transducer with the resonant or resonance frequency thereof changed after a controllable amount of time delay has passed since the drive signal was generated. The transmitting step and the receiving step are carried out a number of times with the time delay changed each time. And the propagation time of the ultrasonic wave is obtained based on the time delay that makes the receiving ultrasonic transducer receive an ultrasonic wave with the highest signal intensity, and the distance to the object of measurement is calculated based on the propagation time.

Another ultrasonic range finding method according to the present invention includes the steps of: transmitting a first ultrasonic wave toward an object of measurement a number of times by driving a transmitting ultrasonic transducer with a first drive signal, which is frequency-modulated and generated a number of times at a predetermined time interval, applied thereto and with its resonant or resonance frequency changed substantially in sync with the frequency modulation of the first drive signal; receiving a first reflected wave, resulting from the first ultrasonic wave that has been reflected from the object of measurement, with the resonant or resonance frequency changed after a predetermined amount of time delay has passed since the first drive signal was generated each time; and calculating the distance to the object of measurement by obtaining the propagation time of the first ultrasonic wave based on the intensity of a first received signal, produced when the first reflected wave is received each time. One of the time interval in the transmitting step and the time delay in the receiving step is fixed and the other is changed.

In one preferred embodiment, the time interval is changed in the transmitting step and the time delay is fixed in the receiving step.

In an alternative preferred embodiment, the time interval is fixed in the transmitting step and the time delay is changed in the receiving step.

In another preferred embodiment, the calculating step includes detecting the intensity of the first reflected wave every time the wave is received, locating the barycenter of the intensity on the axis of time delay based on the intensity detected, and calculating the propagation time of the first ultrasonic wave with respect to the barycenter.

In another preferred embodiment, the method further includes, before the transmitting step, the steps of: transmitting a second ultrasonic wave toward the object of measurement by generating a second drive signal, which switches a first frequency into a second frequency, and driving the transmitting ultrasonic transducer with its resonant or resonance frequency changed substantially in sync with a variation in the frequency of the second drive signal; and receiving a second reflected wave, resulting from the second ultrasonic wave, by driving the receiving ultrasonic transducer such that resonance is produced at the first frequency. A variation in the intensity of a second received signal representing the second reflected wave is detected and the time delay is set based on results of detection.

According to the present invention, while the resonant frequency of an ultrasonic transducer is changed, a frequency-modulated ultrasonic wave is transmitted and received. That is why even if the piezoelectric element of the ultrasonic transducer has a narrow band, the ultrasonic wave can still be transmitted and received in a sufficiently broad range. Consequently, measurements can be done highly accurately without being easily affected by various fluctuations in the measuring environment including noise and wind.

Also, an ultrasonic transducer according to the present invention uses a narrow-band piezoelectric element and has its resonant or resonance frequency changed by an actuator. As a result, the piezoelectric element can be driven with small power and can produce vibrations in a broad range where the piezoelectric element should be driven with high power according to a conventional technique.

BRIEF DESCRIPTION OF THE DRAWINGS

FIG. 1 is a block diagram showing a configuration for a conventional ultrasonic distance measure.

DETAILED DESCRIPTION OF PREFERRED EMBODIMENTS

Embodiment 1

Figure 2A:
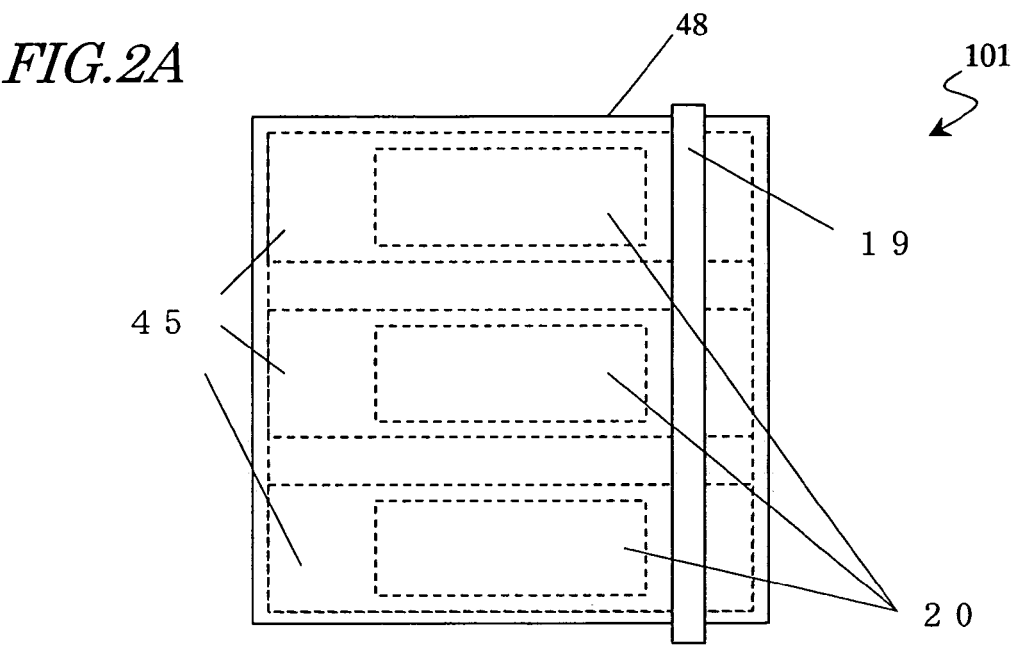
FIGS. 2A and 2B are respectively a plan view and a cross-sectional view of an ultrasonic transducer for use in an ultrasonic distance measure according to the present invention.
Figure 2B:
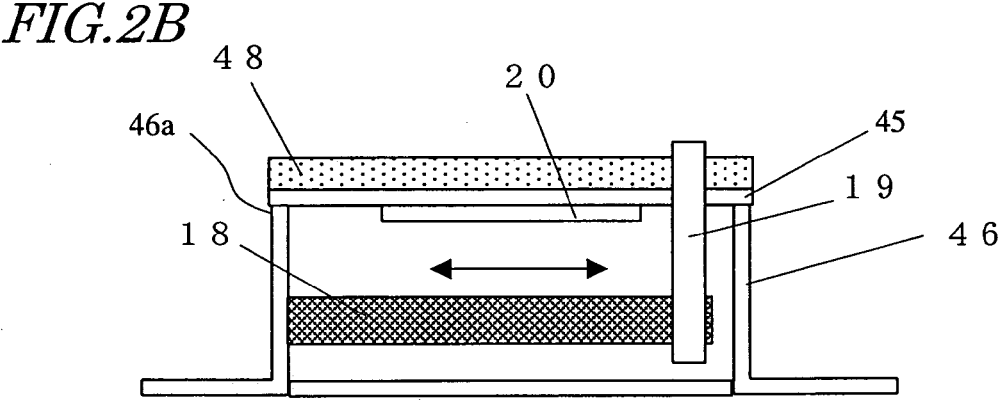

First, an ultrasonic transducer for use in an ultrasonic distance measure according to the present invention will be described. FIGS. 2A and 2B are respectively a top view and a side view of an ultrasonic transducer 101. The ultrasonic transducer 101 includes a diaphragm 45, piezoelectric transducers 20, an actuator 18 and a case 46. The piezoelectric transducers 20 are attached to the diaphragm 45 and the case 46 supports one end of the diaphragm 45 on a supporting portion 46a. A supporting plate 19 is provided near another end of the diaphragm 45. Both ends of the actuator 18 are fixed to the case 46 and the supporting plate 19, respectively. Optionally, an acoustic matching layer 48 may be provided on the surface of the diaphragm 45.

The piezoelectric transducers 20 are made of a piezoelectric ceramic such as lead zirconate titanate (PZT) and produce vibrations at a frequency in an ultrasonic range (e.g., at a frequency of approximately 20 kHz or more) upon the application of a voltage thereto. Any of various conventional ultrasonic transducers that have been used in ultrasonic distance measures, ultrasonic sensors and so on may be adopted as the ultrasonic transducers 20.

The actuator 18 may be made of a stacked piezoelectric ceramic, for example. And when a DC voltage is applied as a control voltage thereto, the actuator 18 either expands or shrinks in the directions pointed by the arrow according to the polarity and magnitude of the voltage applied. As long as the applied voltage is maintained, the actuator 18 keeps the same length. As a result, the supporting plate 19 secured to the actuator 18 either stretches or shrinks the diaphragm 45.

When a drive voltage is applied thereto, the piezoelectric transducers 20 attached to the diaphragm 45 produce vibrations in a vibration mode and at a resonant frequency that are determined by the material of the piezoelectric transducers 20 and the shapes of the piezoelectric transducers 20 and the diaphragm 45. In this preferred embodiment, the piezoelectric transducers 20 vibrate in such a flexure mode as to produce nodes near the ends of the diaphragm 45. When a DC voltage is applied to the actuator 18, the diaphragm 45 either stretches or shrinks to change this resonant frequency. The resonant frequency changes continuously according to the magnitude of displacement of the actuator 18.

In the ultrasonic distance measure of the present invention, such ultrasonic transducers 101 are used as the transmitting and receiving ultrasonic transducers. In transmitting a frequency-modulated ultrasonic wave, the piezoelectric transducers 20 are driven with a voltage applied to the actuator 18, thereby changing the resonant frequency with the variation in the modulated frequency. As a result, the operating range of the ultrasonic transducer can be expanded and the distance can be measured accurately with the frequency-modulated drive signal. Also, by receiving the frequency-modulated ultrasonic wave with the timing of applying the voltage to the actuator 18 changed, the variation in the signal intensity of the received signal is monitored.

The ultrasonic transducer 101 vibrates the air by bonding the piezoelectric transducers 20 to the diaphragm 45. Alternatively, the diaphragm 45 and the piezoelectric transducers 20 may be replaced with a bimorph type piezoelectric transducer in which two piezoelectric bodies are bonded together. Also, in the ultrasonic distance measure of the present invention, not only the ultrasonic transducer 101 but also an ultrasonic transducer with any of various structures for transmitting and receiving an ultrasonic wave with the resonant or resonance frequency changed may be adopted as well.

Figure 3A:
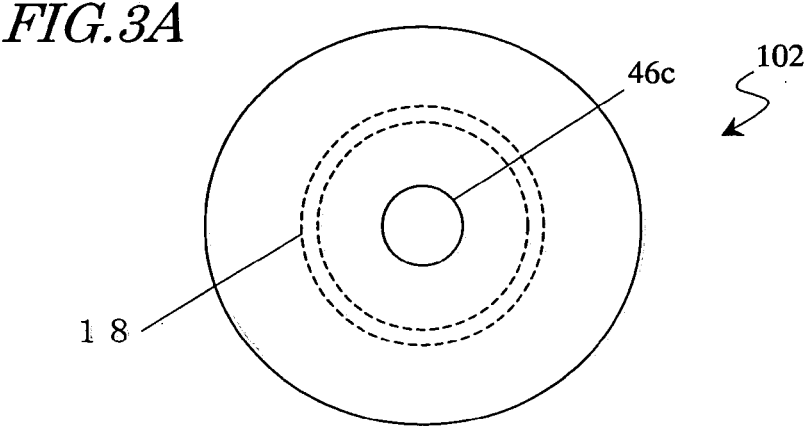
FIGS. 3A and 3B are respectively a plan view and a cross-sectional view of another ultrasonic transducer for use in an ultrasonic distance measure according to the present invention.
Figure 3B:
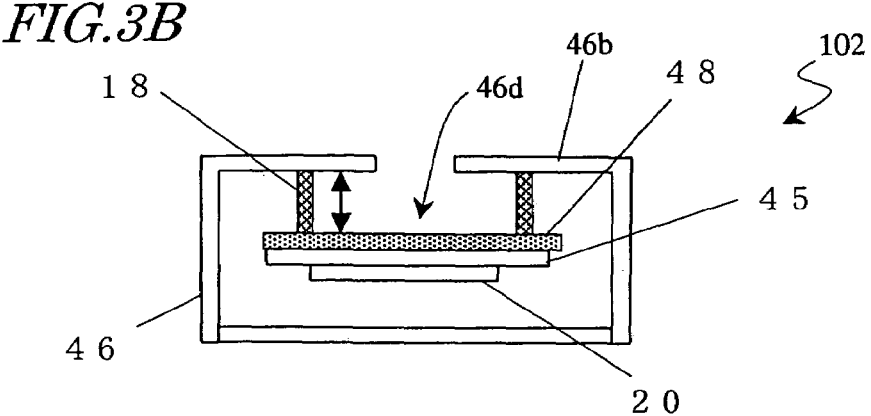

The ultrasonic transducer 102 shown in FIGS. 3A and 3B includes a piezoelectric transducer 20, a diaphragm 45, an acoustic matching layer 48, an actuator 18 and a case 46. The piezoelectric transducer 20, diaphragm 45 and acoustic matching layer 48 are stacked one upon the other such that the diaphragm 45 is sandwiched between the piezoelectric transducer 20 and the acoustic matching layer 48. The actuator 18 has a cylindrical shape and the acoustic matching layer 48 is bonded to one end of that cylinder. The other end of the cylinder is secured to the inner surface of the top 46b of the case 46 and the top 46b has a hole 46c. The space formed by the actuator 18, acoustic matching layer 48 and top 46b defines a resonator 46d.

When a drive voltage is applied to the piezoelectric transducer 20, the piezoelectric transducer 20 starts to vibrate in either a spread vibration mode or a thickness vibration mode. As a result, the acoustic matching layer 48 vibrates at a resonance frequency determined by the size of the resonator 46d, thereby producing an ultrasonic wave.

When a DC voltage is applied, the actuator 18 stretches or shrinks in the direction pointed by the arrow. Consequently, the size and the resonance frequency of the resonator 46d both change.

Figure 4:
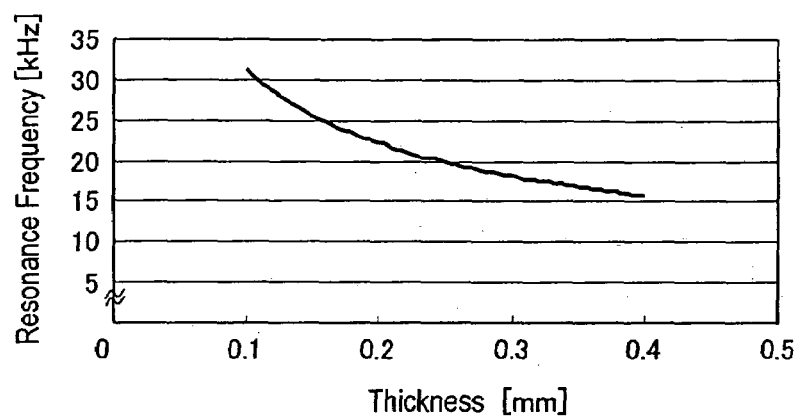
FIG. 4 is a graph showing the vibration characteristic of the ultrasonic transducer shown in FIG. 3.

FIG. 4 shows how the resonance frequency changes with the size of the actuator 18. As shown in FIG. 4, if the length of the actuator 18 changes from 0.4 mm to 0.1 mm, the resonance frequency changes by about 15 kHz.

Figure 5:
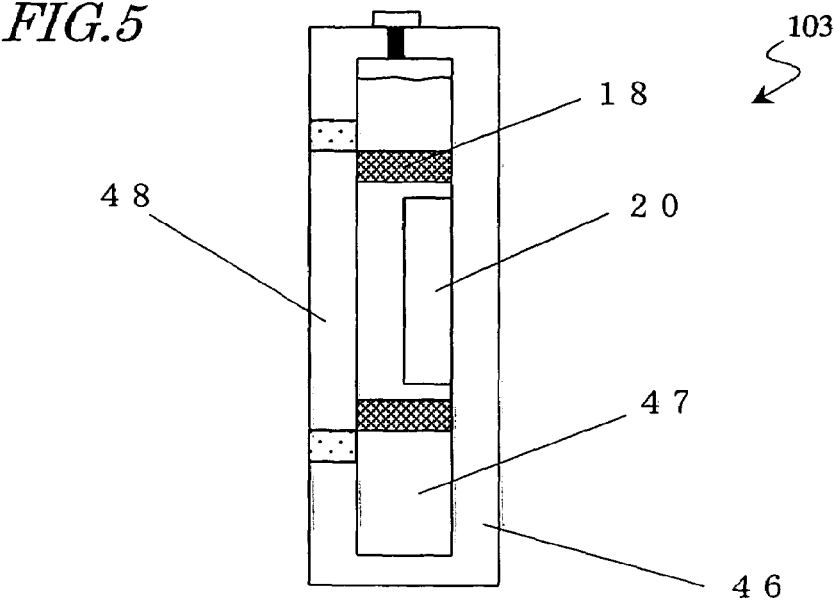
FIG. 5 is a cross-sectional view of another ultrasonic transducer for use in an ultrasonic distance measure according to the present invention.

Furthermore, the ultrasonic transducer 103 shown in FIG. 5 includes a case 46, a piezoelectric transducer 20, an actuator 18, a first acoustic matching layer 48 and a second acoustic matching layer 47. The first acoustic matching layer 48 is fit into one side surface of the case 46 and the piezoelectric transducer 20 is held in the case 46 so as to face the first acoustic matching layer 48. The second acoustic matching layer 47 is a liquid that fills at least the gap (i.e., is interposed) between the first acoustic matching layer 48 and the piezoelectric transducer 20. The liquid that can be used as the second acoustic matching layer 47 is preferably an inactive solution such as Florinate. Alternatively, water, alcohol or any other liquid may also be used unless the actuator 18, piezoelectric transducer 20 or a line for applying a voltage to these members is affected (e.g., corroded).

When a DC voltage is applied, the actuator 18 either stretches or shrinks, thereby changing the gap between the first acoustic matching layer 48 and the piezoelectric transducer 20. As a result, the thickness of the second acoustic matching layer 47 and the resonant frequency of the ultrasonic transducer 103 can be changed.

Figure 6:
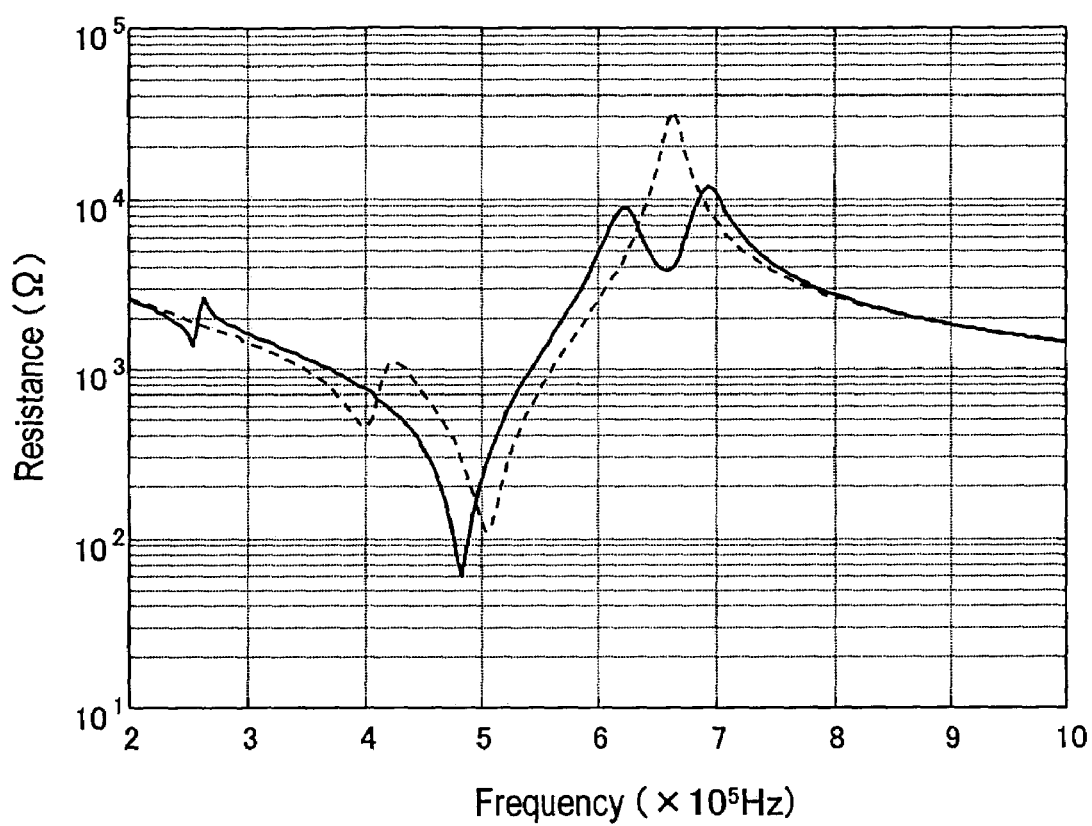
FIG. 6 is a graph showing the vibration characteristic of the ultrasonic transducer shown in FIG. 5.
Figure 7:
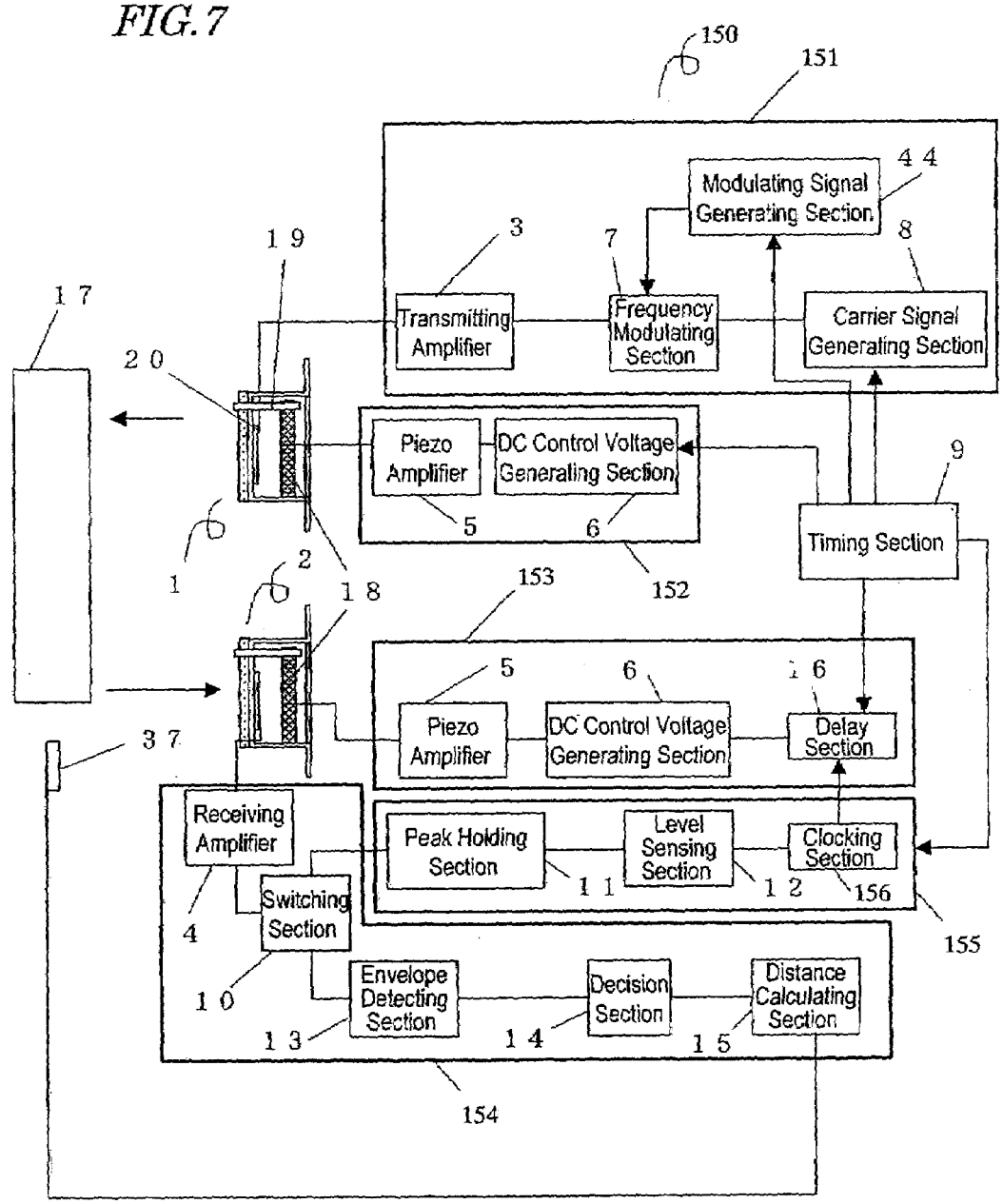
FIG. 7 is a block diagram showing a configuration for a first preferred embodiment of an ultrasonic distance measure according to the present invention.

FIG. 6 is a graph showing how the resonant frequency may be changed by the ultrasonic transducer 103. In the example shown in FIG. 6, the ultrasonic transducer 103 includes a piezoelectric transducer 20 made of PZT, a first acoustic matching layer 48 made of a material obtained by molding together glass balloons with an epoxy resin, and a second acoustic matching layer 47 made of Florinate. If the thickness of the second acoustic matching layer 47 is changed from 0.4 mm to 0.1 mm, then the resonant frequency changes by about 30 kHz from 470 kHz to 500 kHz as shown in FIG. 6. Hereinafter, an ultrasonic distance measure according to this preferred embodiment will be described. As shown in FIG. 7, the ultrasonic distance measure 150 includes a transmitting ultrasonic transducer 1, a receiving ultrasonic transducer 2, a driving section 151, a transmitting control voltage generating section 152, a receiving control voltage generating section 153, a receiving section 154 and a propagation time premeasuring section 155. The ultrasonic distance measure 150 further includes a timing section 9 for generating a trigger signal that sets a timing to transmit the ultrasonic wave from the transmitting ultrasonic transducer 1.

As the transmitting and receiving ultrasonic transducers 1 and 2, ultrasonic transducers, of which the resonant or resonance frequencies are changeable, are used. For example, the ultrasonic transducers 101, 102, 103 described above can be used effectively. In this preferred embodiment, the ultrasonic transducers 101 are used.

Figure 8:
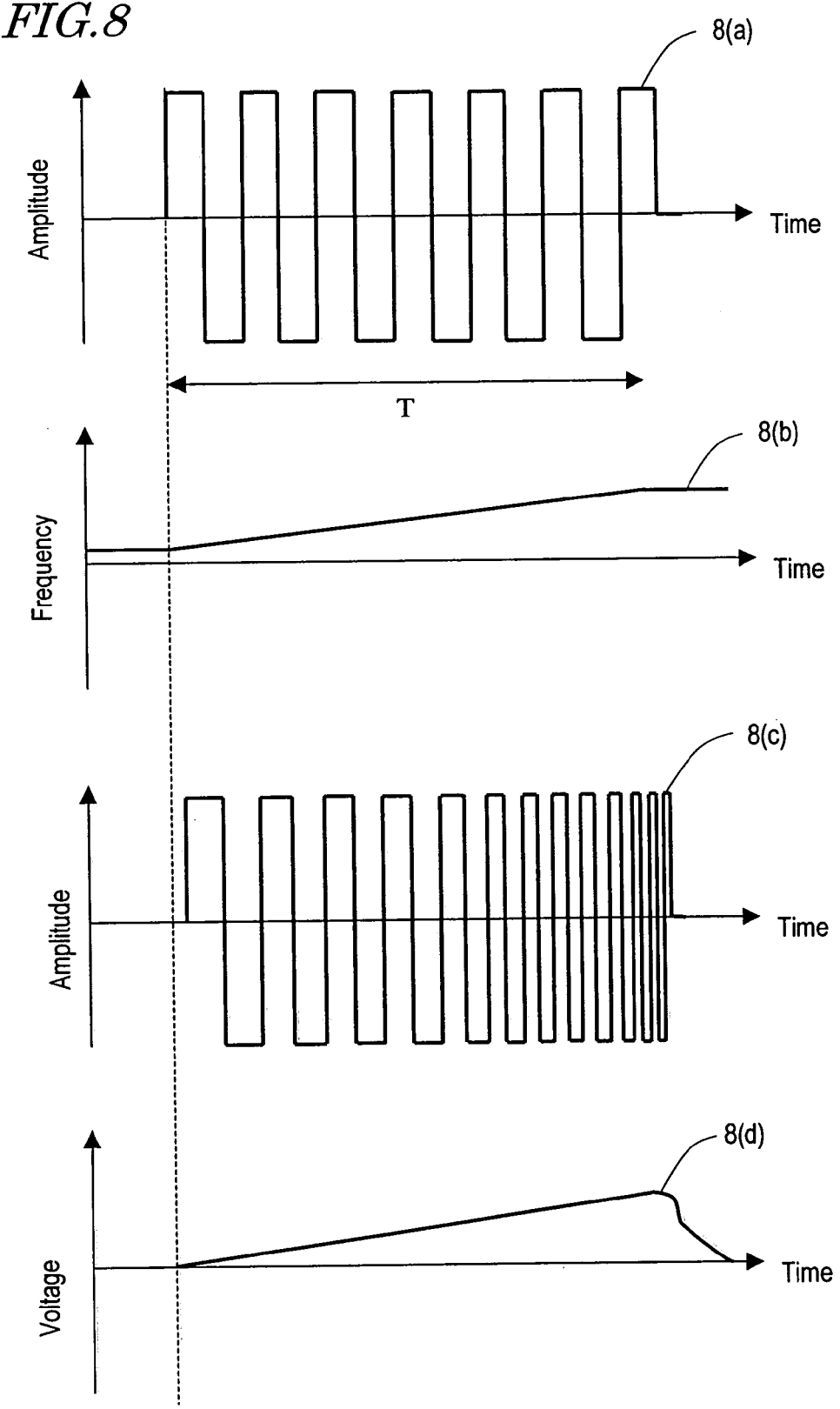
FIG. 8 shows exemplary waveforms of signals generated by respective components of the driving section of the ultrasonic distance measure shown in FIG. 7.

The driving section 151 generates a frequency-modulated drive signal to drive the transmitting ultrasonic transducer 1 and transmit an ultrasonic wave, and applies the drive signal generated to the transmitting ultrasonic transducer 1. The driving section 151 preferably includes a carrier signal generating section 8, a modulating signal generating section 44, a frequency modulating section 7 and a transmitting amplifier 3. FIG. 8 shows the signals generated in the driving section 151. The carrier signal generating section 8 generates a drive signal that produces vibrations in the transmitting ultrasonic transducer 1. The modulating signal generating section 44 produces a modulating frequency for the purpose of frequency modulation. For example, as shown in FIG. 8, the carrier signal generating section 8 generates a carrier signal 8(a) as a rectangular wave with a frequency of 15 kHz and the modulating signal generating section 44 generates a modulating signal 8(b) of which the frequency changes from 15 kHz to 30 kHz in a period of 400 ms.

The frequency modulating section 7 modulates the carrier signal with the modulating signal, thereby outputting a frequency-modulated carrier signal to the transmitting amplifier 3. In response, the transmitting amplifier 3 amplifies the received signal and outputs the drive signal 8(c) shown in FIG. 8 to the transmitting ultrasonic transducer 1. To generate the two signals synchronously with each other, the carrier signal generating section 8 and the modulating signal generating section 44 generate the carrier signal and the modulating signal in response to the trigger signal supplied from the timing section 9.

The transmitting control voltage generating section 152 generates a control voltage that changes the resonant or resonance frequency of the transmitting ultrasonic transducer 1. For that purpose, the transmitting control voltage generating section 152 includes a DC control voltage generating section 6 and a piezo amplifier 5. On receiving the trigger signal from the timing section 9, the DC control voltage generating section 6 generates a DC control voltage to drive the actuator. The piezo amplifier 5 amplifies the DC control voltage and applies the amplified control voltage to the actuator 18 of the transmitting ultrasonic transducer 1.

The DC control voltage applied to the actuator 18 has its profile defined in advance such that the resonant or resonance frequency of the transmitting ultrasonic transducer 1 changes substantially in sync with the modulation of the frequency of the drive signal. For example, a DC control voltage such as that shown in FIG. 8, which starts to be applied when the drive signal 8(c) is output and of which the voltage level increases as the modulated frequency changes but decreases once the drive signal is stopped, is applied to the actuator 18. When the DC control voltage is applied to the actuator 18, the resonant frequency of the transmitting ultrasonic transducer 1 changes with the modulated frequency. The transmitting ultrasonic transducer 1 transmits an ultrasonic wave in response to the drive signal while changing its resonant frequency.

The ultrasonic wave transmitted from the transmitting ultrasonic transducer 1 travels toward, and then is reflected by, an object 17 of measurement. The reflected ultrasonic wave then reaches the receiving ultrasonic transducer 2 and is converted by the receiving ultrasonic transducer 2 into an electrical signal. In this case, the receiving ultrasonic transducer 2 receives the reflected wave while changing the resonant frequency.

The receiving control voltage generating section 153 includes a piezo amplifier 5, a DC control voltage generating section 6 and a delay section 16 to generate a control voltage that changes the resonant or resonance frequency of the receiving ultrasonic transducer 2. The piezo amplifier 5 and DC control voltage generating section 6 may have the same configurations as the counterparts of the transmitting control voltage generating section 152. However, the DC control voltage generating section 6 on the receiving end generates the DC control voltage in response to the output signal of the delay section 16, not the trigger signal supplied from the timing section 9.

The delay section 16 receives the trigger signal from the timing section 9 and estimated propagation time information from a clocking section 156 to be described later. Whenever receiving the trigger signal, the delay section 16 causes a time delay, of which the length is different from the previous one by $\Delta t$. And when that amount of time delay has passed, the delay section 16 will output a signal to the DC control voltage generating section 6. When the intensity of the received reflected wave reaches a predetermined sensing level, the ultrasonic distance measure 150 acknowledges the sensing of the reflected wave and defines the arrival time of the reflected wave. Accordingly, supposing the estimated propagation time of the reflected wave is $\Delta T_0$, very low level portions of the received wave have already reached the receiving ultrasonic transducer 2 before $\Delta T_0$ passes. For that reason, the received signal should start being detected at a time $\Delta T_0-\alpha$, which is earlier than $\Delta T_0$ by $\alpha$. If the ultrasonic wave is repeatedly transmitted and received a number of times by outputting the trigger signal 2n+1 times (where n is an integer that is equal to or greater than one) and if the estimated propagation time is $\Delta T_0$, then the time delays caused will be $\Delta T_0-a-n\Delta t$, $\Delta T_0-a-(n-1)\Delta t$, $\Delta T_0-a-(n-2)\Delta t$, ..., $\Delta T_0-a-2\Delta t$, $\Delta T_0-a-\Delta t$, $\Delta T_0-a$, $\Delta T_0-a+\Delta t$, ... and $\Delta T_0-a+n\Delta t$.

In the receiving control voltage generating section 153, every time the delay section 16 receives the trigger signal, the DC control voltage generating section 6 generates the DC control voltage at a timing different from the previous one by $\Delta t$ and the piezo amplifier 5 amplifies the DC control voltage generated and applies it to the actuator 18 of the receiving ultrasonic transducer 2.

Figure 9:
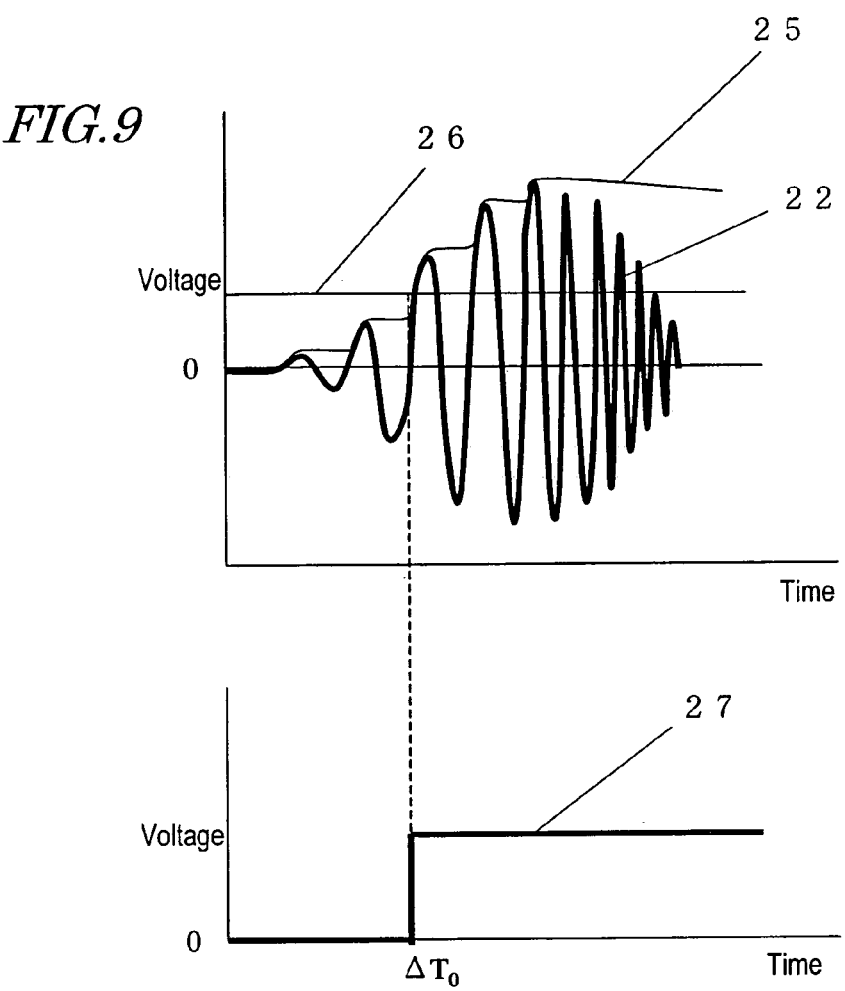
FIG. 9 shows how the propagation time premeasuring section of the ultrasonic distance measure shown in FIG. 7 detects a received signal.

The receiving section 154 includes a receiving amplifier 4, a switching section 10, an envelope detecting section 13, and a decision section 14. The receiving, amplifier 4 amplifies the received signal that has been converted by the receiving ultrasonic transducer 2. The switching section 10 switches the destinations of the signal repeatedly received such that only the signal received for the first time is output to the propagation time premeasuring section 155 and every signal received after that is output to the envelope detecting section 13. When the receiving section 154 receives the first signal, the received signal is output to the propagation time premeasuring section 155. The propagation time premeasuring section 155 includes a peak holding section 11, a level sensing section 12 and a clocking section 156. The received signal is input to the peak holding section 11 first. FIG. 9 shows the signals in respective sections of the propagation time premeasuring section 155. The peak holding section 11 holds the peak values of the first received signal 22 and outputs a peak value signal 25 to the level sensing section 12. The level sensing section 12 compares the peak value signal 25 to a predetermined threshold value 26. When the peak value signal 25 exceeds the threshold voltage 26, the level sensing section 12 outputs a sensing signal 27. The clocking section 156 receives the trigger signal from the timing section 9 and the sensing signal 27. The clocking section 156 measures the interval between the reception time of the trigger signal and that of the sensing signal 27, and outputs the interval measured as the estimated propagation time $\Delta T_0$ to the delay section 16 of the receiving control voltage generating section 153.

As described above, in a period of time of which the center is defined by the estimated propagation time $\Delta T0$ minus the time $\alpha$, the delay section 16 causes a time delay, of which the length is different from the previous one by $\Delta t$, on receiving the trigger signal from the timing section 9 every time, and outputs a signal to the DC control voltage generating section 6 after that amount of time delay has passed. As a result, every time an ultrasonic wave is transmitted from the transmitting ultrasonic transducer 1, the receiving ultrasonic transducer 2 receives a reflected wave while being applied with a DC control voltage at a different timing.

Figure 10A:
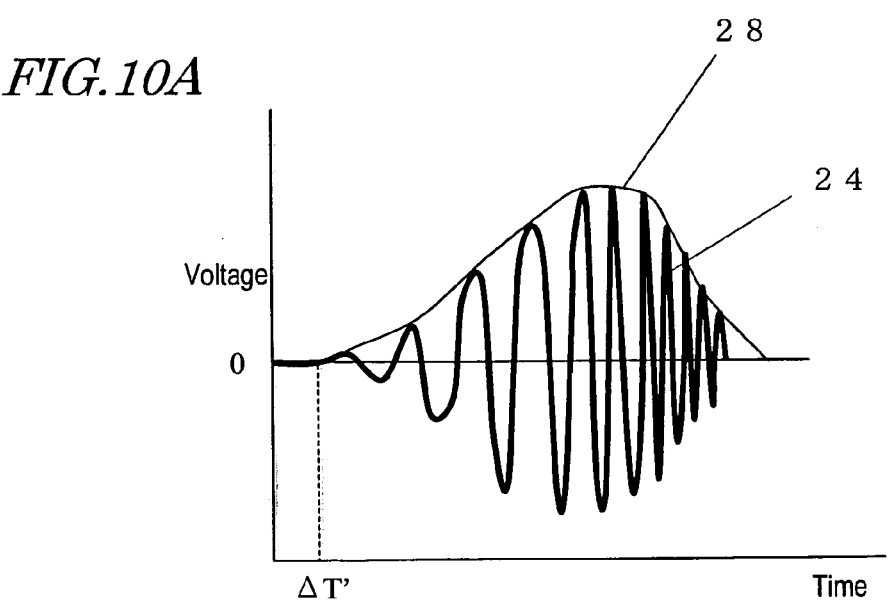
FIG. 10A shows an exemplary signal received at a receiving section and an envelope signal thereof.
Figure 10B:
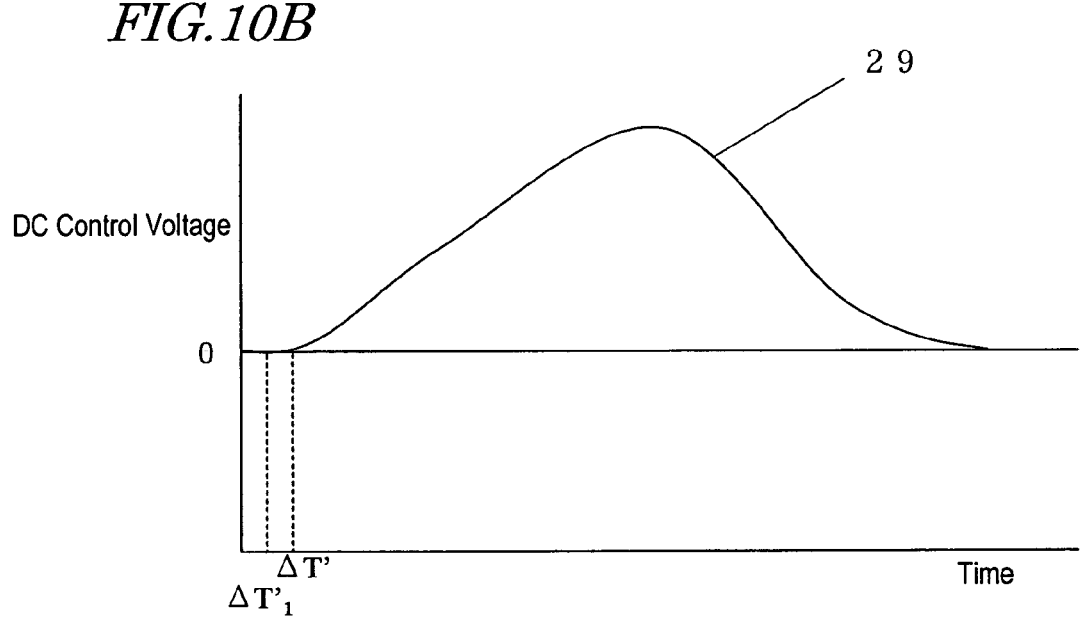
FIG. 10B shows a control voltage applied to the receiving ultrasonic transducer when the received signal shown in FIG. 10A is detected.

Every signal received by the receiving section 154 after that is output to the envelope detecting section 13. FIG. 10A shows the envelope 28 of the received signal 24 generated by the envelope detecting section 13. FIG. 10B shows the profile 29 of the DC control voltage generated by the receiving control voltage generating section 153 when that received signal 24 is received. In FIGS. 10A and 10B, the origin is $\Delta T_0-\alpha$. As shown in FIGS. 10A and 10B, the received signal rises at a time $\Delta T'$, showing that the reflected wave arrived at the time $\Delta T'$. On the other hand, the DC control voltage is generated at a time $\Delta T'1$, which is ahead of $\Delta T'$, and is applied to the actuator 18.

Figure 11A:
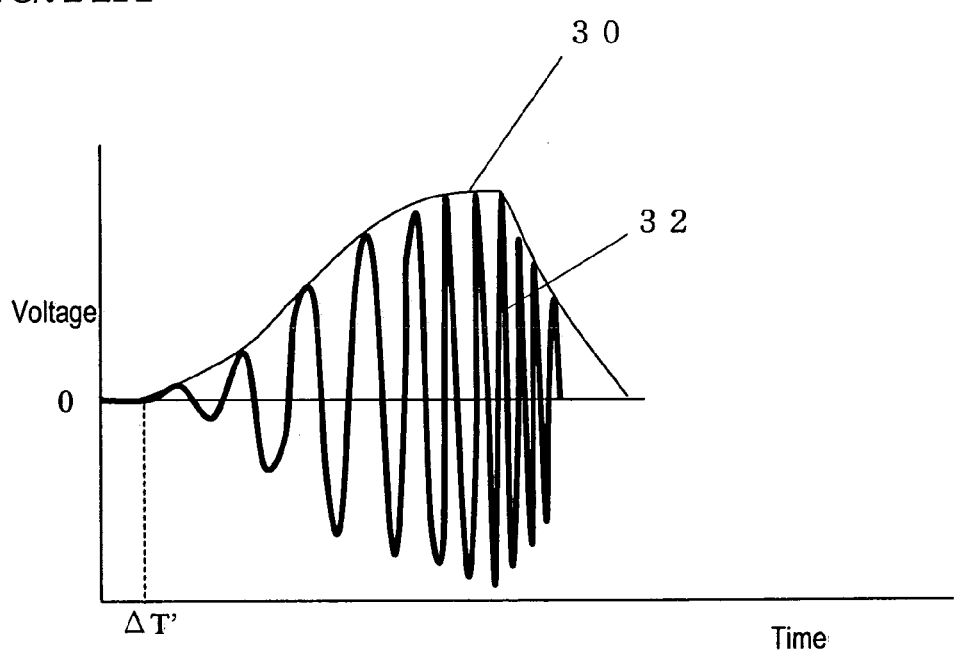
FIG. 11A shows another exemplary signal received at the receiving section and an envelope signal thereof.
Figure 11B:
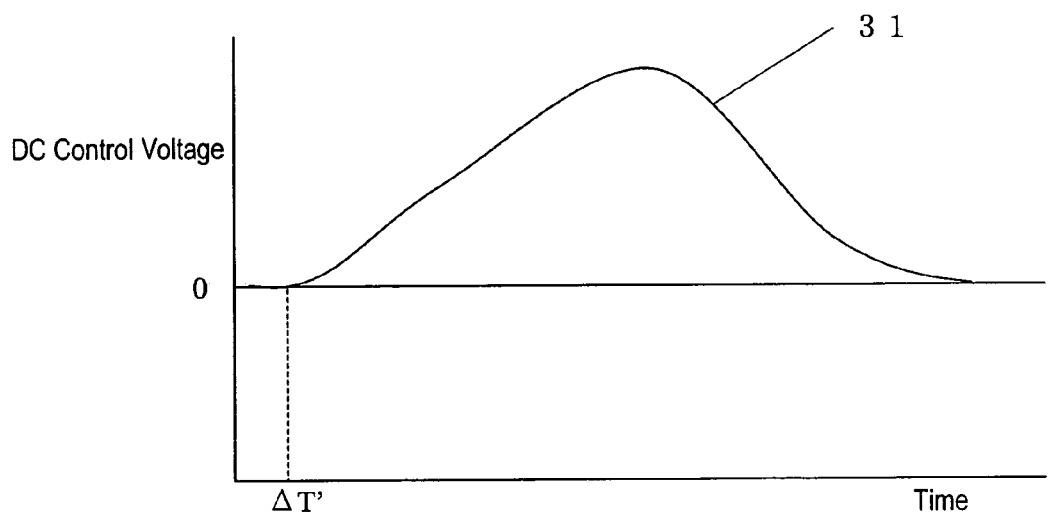
FIG. 11B shows a control voltage applied to the receiving ultrasonic transducer when the received signal shown in FIG. 11A is detected.

FIG. 11A shows an envelope 30 obtained by getting another received signal 32 detected by the envelope detecting section 13. FIG. 11B shows the profile 31 of the DC control voltage generated by the receiving control voltage generating section 153 when that received signal 32 is received. As shown in FIGS. 11A and 11B, the received signal rises at a time $\Delta T'$, showing that the reflected wave arrived at the time $\Delta T'$. On the other hand, the DC control voltage is generated at a time $\Delta T'_2$, which agrees with the time $\Delta T'$, and is applied to the actuator 18.

Every time the ultrasonic wave is repeatedly transmitted and received on and after the second time, the transmission of the ultrasonic wave from the transmitting ultrasonic transducer 1 is synchronous with the generation of the trigger signal at the timing section 9. Also, in the transmitting ultrasonic transducer 1, the DC control voltage is applied to the actuator 18 synchronously with the frequency modulation of the drive signal. That is to say, the ultrasonic waves to be transmitted a number of times are generated by reference to the trigger signal and have the same waveform.

If the object 17 of measurement never moved during the measurement, then each reflected wave would arrive at the receiving ultrasonic transducer 2 in a constant amount of time after the trigger signal was applied and would always have the same waveform. However, the DC control voltage is applied to the actuator 18 of the receiving ultrasonic transducer 2 so as to rise in a predetermined amount of time after the trigger signal has risen (i.e., such that each rise of the DC control voltage shifts from an associated rise of the trigger signal) as described above. If the time when the reflected wave reaches the receiving ultrasonic transducer 2 most closely matches the time when the DC control voltage is applied to the actuator 18, then the resonant frequency of the receiving ultrasonic transducer 2 changes synchronously with the modulated frequency of the reflected wave. As a result, the received signal has increased amplitude. In other words, the envelope obtained at the envelope detecting section 13 has an increased integrated area.

Figure 12:
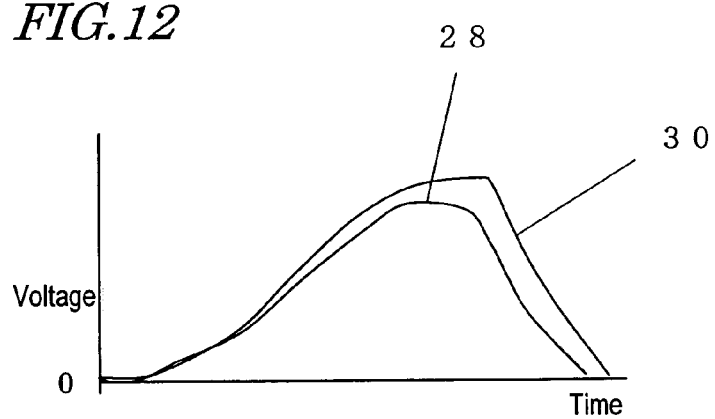
FIG. 12 shows the envelope signals shown in FIGS. 10A and 11A with those signals superposed on upon the other.

FIG. 12 shows the envelopes shown in FIGS. 10A and 11A with the envelope 30 shown in FIG. 11 superposed on the envelope 28 shown in FIG. 10. As is clear from FIG. 12, the envelope 30 has a greater integrated area than the envelope 28. The difference is even more noticeable in the latter half of the received signal in which the frequency has been increased as a result of the modulation. This means that the variation in the resonant frequency of the receiving ultrasonic transducer 2 matched more closely the modulation in the frequency of the reflected wave when the received signal resulting in the envelope 30 was received.

Figure 13:
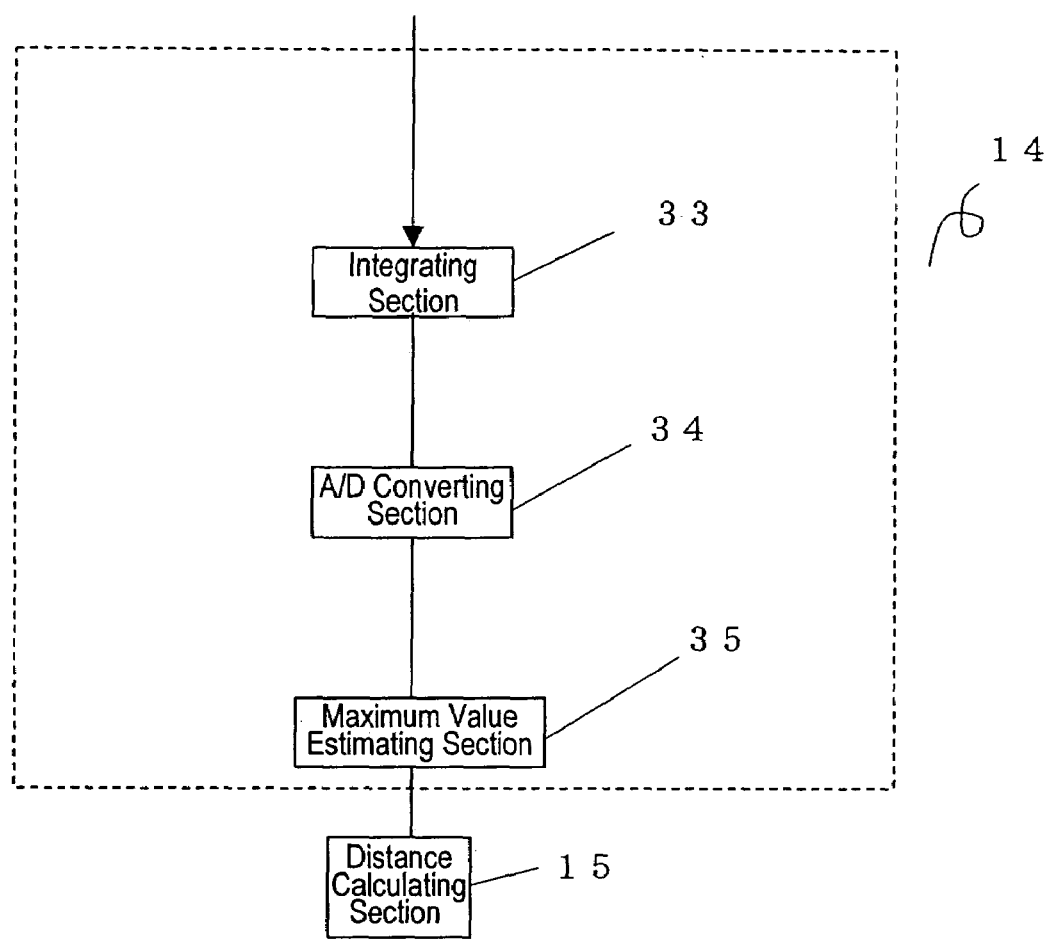
FIG. 13 is a block diagram showing a configuration for the decision section.

To make such a decision, the decision section 14 includes an integrating section 33, an A/D converting section 34 and a maximum value estimating section 35 as shown in FIG. 13. Every time the envelope of a received signal is detected, the integrating section 33 integrates the envelope and then the A/D converting section 34 converts the resultant integrated value into a digital value. The maximum value estimating section 35 receives information about the time delay and the number of times of repetition from the delay section 16. When the integrated values are obtained the same number of times as that of repetition, the maximum value estimating section 35 finds a time delay that is associated with the maximum digital integrated value thereof. In this manner, the maximum value estimating section 35 figures out the propagation time and outputs it to the distance calculating section 15. The propagation time may be directly calculated from the time delay that maximizes the integrated value. Alternatively, the resultant integrated values may be interpolated and the maximum integrated value and a time delay associated with that integrated value may be estimated, too. If no interpolation is carried out, then the interval of the time delays defines the accuracy of measurement.

The distance calculating section 15 calculates the distance to the object of measurement 17 based on the estimated propagation time and the velocity of the ultrasonic wave. The environmental temperature around the object of measurement 17 may be measured with a thermometer 37 as shown in FIG. 7 and the velocity of the ultrasonic wave may be corrected with the environmental temperature. The sonic velocity v (m) in the air may be approximated as a function of the temperature t (° C.) as v=331.45+0.6 (t). By correcting the propagation velocity of the ultrasonic wave in accordance with this equation, the distance can be calculated more accurately.

Hereinafter, it will be described with reference to FIG. 14 and FIGS. 15 through 18 how to measure the distance using this ultrasonic distance measure 150.

Figure 14:
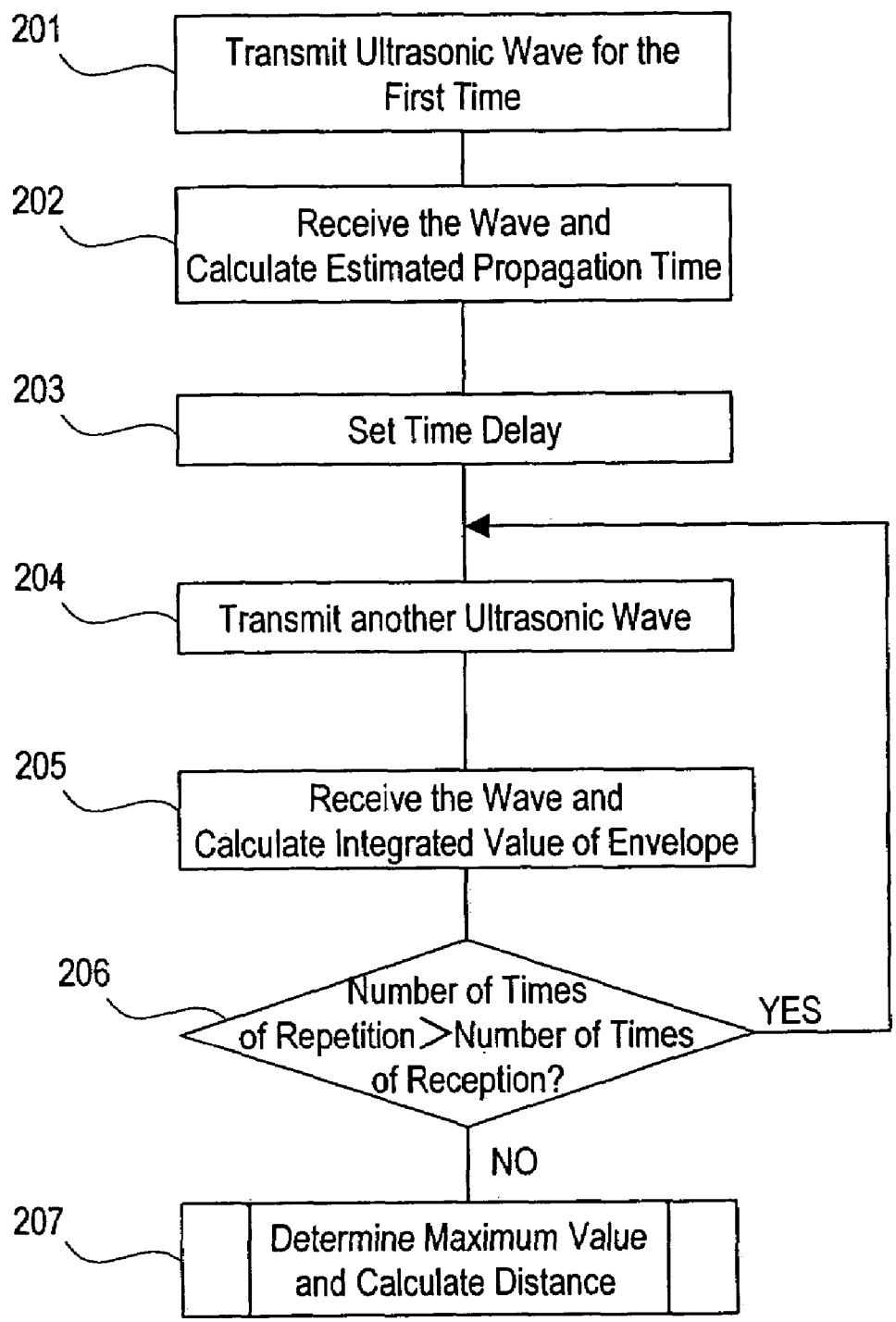
FIG. 14 is a flowchart showing a procedure of measuring.
Figure 15:
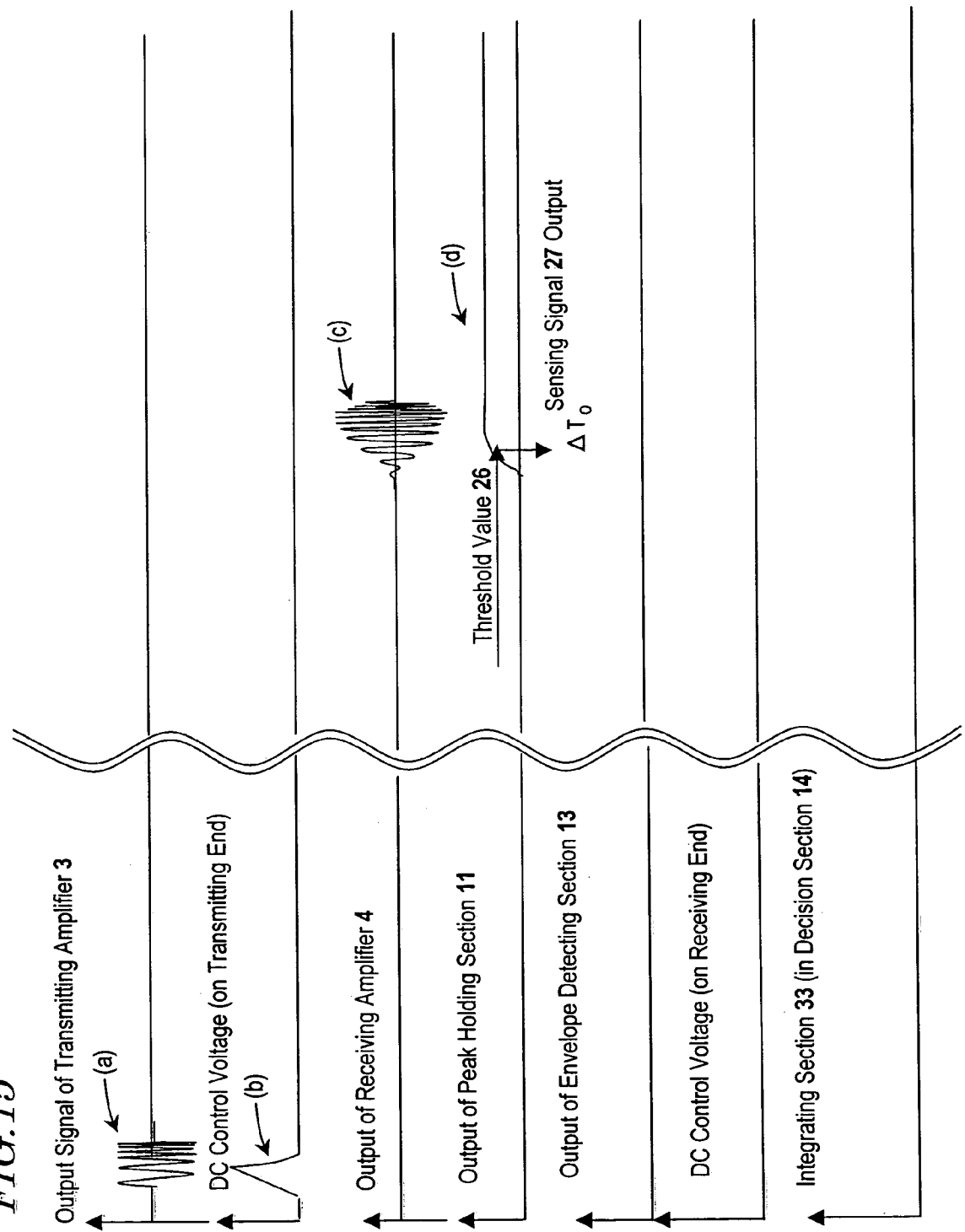
FIG. 15 is an exemplary timing diagram showing signals at respective components of the ultrasonic distance measure shown in FIG. 7.

FIG. 14 is a flowchart showing a procedure to measure the distance using the ultrasonic distance measure 150. FIGS. 15 through 18 are timing diagrams showing the waveforms of the drive signal output from the transmitting amplifier 3 of the ultrasonic distance measure 150 (in portion (a)), a signal representing the DC control voltage output from the transmitting control voltage generating section 152 (in portion (b)), the received signal output from the receiving amplifier 4 (in portion (c)), the peak value signal of the peak holding section 11 (in portion (d)), the output signal of the envelope detecting section 13 (in portion (e)), a signal representing the DC control voltage output from the receiving control voltage generating section 153 (in portion (f)), and the integrated signal at the decision section 14 (in portion (g)), which were measured at mutually different points in time during the measurement. First, as shown in FIG. 15, the transmitting section 151 generates a frequency-modulated drive signal (a) and the transmitting ultrasonic transducer 1 is driven with the drive signal while the resonant frequency of the transmitting ultrasonic transducer 1 matched with the modulated frequency of the drive signal using the DC control voltage signal (b) (in Step 201).

The ultrasonic wave transmitted from the transmitting ultrasonic transducer 1 is reflected from the object of measurement 17 and then the reflected wave reaches the receiving ultrasonic transducer 2. The receiving ultrasonic transducer 2 converts the reflected wave into an electrical signal and the receiving amplifier 4 amplifies the electrical signal, thereby obtaining the received signal (c). Then, the propagation time premeasuring section 155 calculates the estimated propagation time based on the received signal (c) (in Step 202). More specifically, the peak values of the received signal (c) are held, thereby generating the peak value signal (d). Next, the peak value signal (d) is compared with a threshold value 26. And when the peak value signal 25 exceeds the threshold value 26, the sensing signal 27 is output. The time when the sensing signal 27 is output is supposed to represent the estimated propagation time $\Delta T_0$. Then, the number of times the transmission and reception is repeatedly carried out and the magnitude of the variation in time delay are determined in Step 203 such that the ultrasonic wave can be transmitted, received and measured during a predetermined period, of which the midpoint is defined by subtracting $\alpha$ from the estimated propagation time $\Delta T_0$.

Next, the timing section 9 generates the trigger signal repeatedly the number of times determined in Step 203. Every time the trigger signal is generated, the ultrasonic wave is transmitted from the transmitting ultrasonic transducer 1. And the receiving ultrasonic transducer 2, to which the receiving DC control voltage has been applied after a predetermined time delay, receives the reflected wave. The receiving section 154 detects the envelope of the received signal thus obtained and calculates the integrated value of the envelope in Steps 204 and 205.

Figure 16:
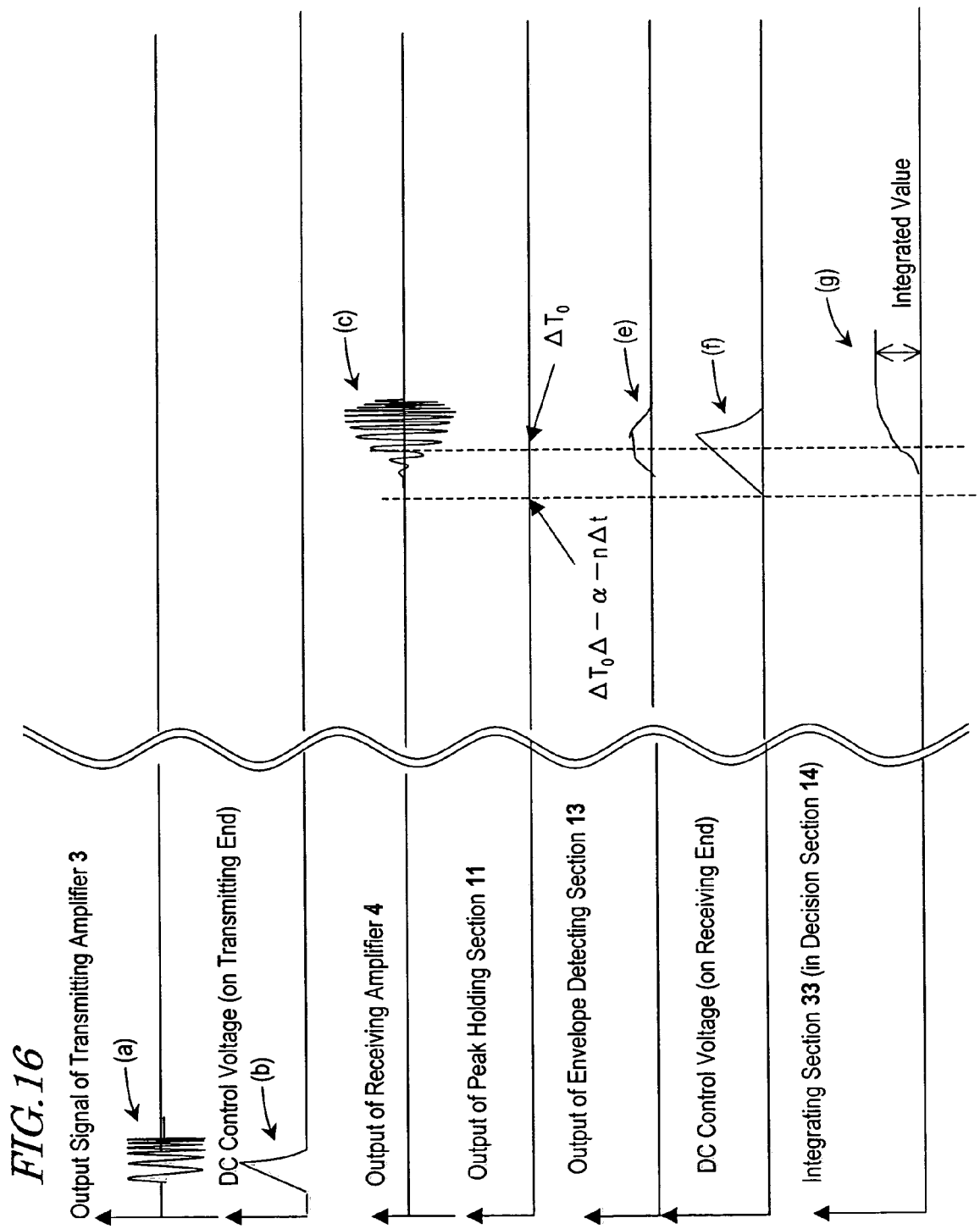
FIG. 16 is another exemplary timing diagram showing signals at the respective components of the ultrasonic distance measure shown in FIG. 7.
Figure 17:
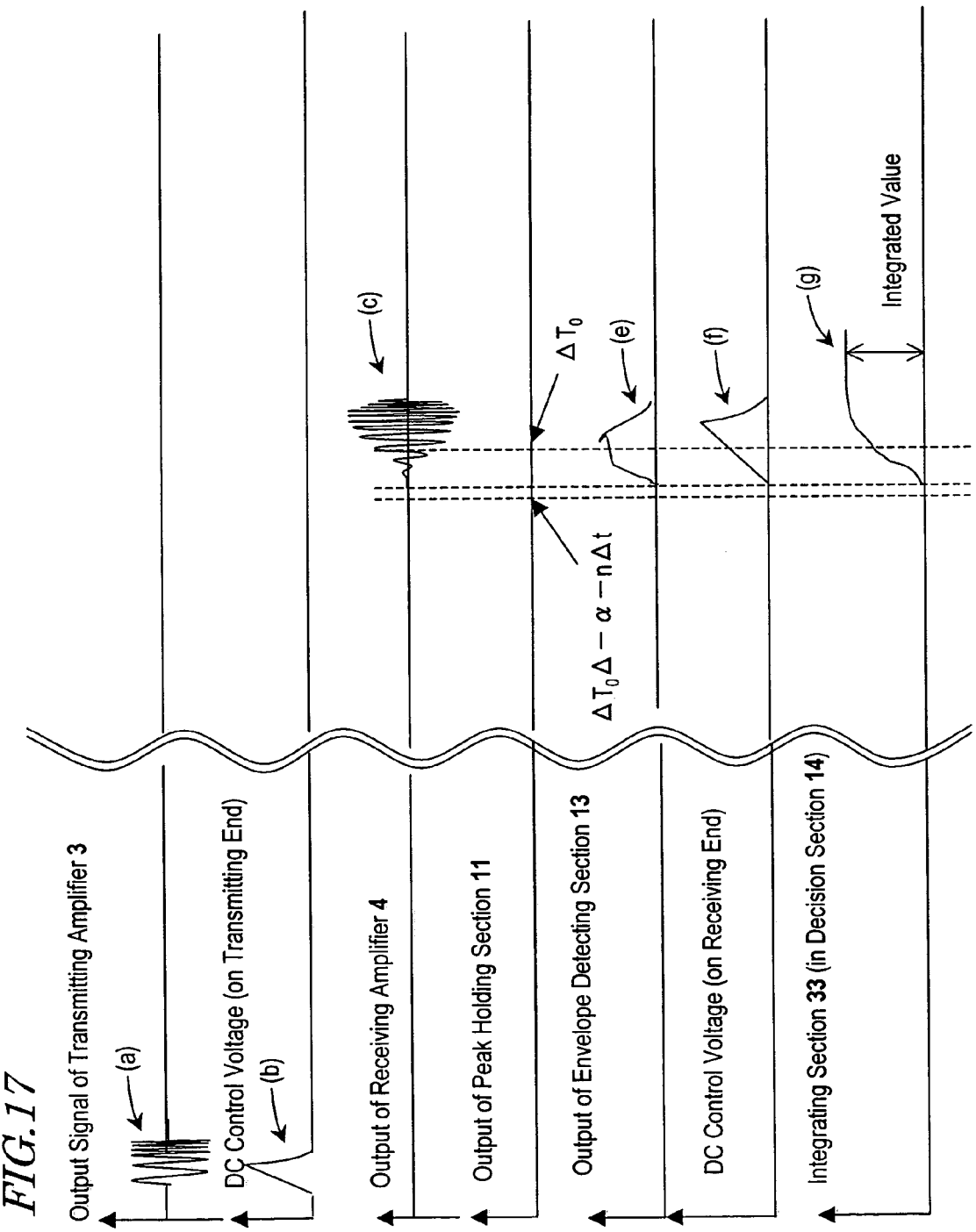
FIG. 17 is another exemplary timing diagram showing signals at the respective components of the ultrasonic distance measure shown in FIG. 7.
Figure 18:
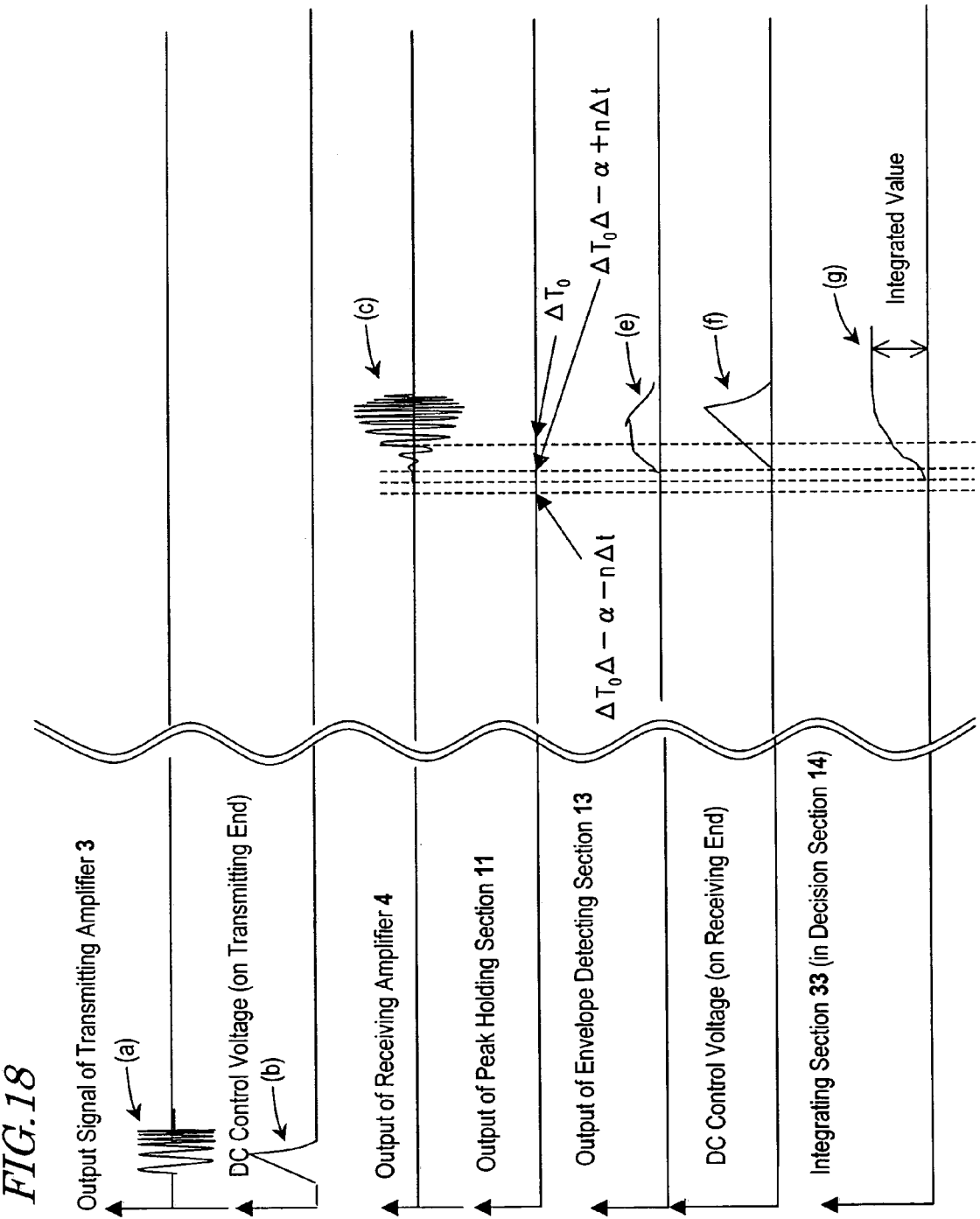
FIG. 18 is another exemplary timing diagram showing signals at the respective components of the ultrasonic distance measure shown in FIG. 7.

The timing diagrams of FIGS. 16, 17 and 18 show a situation where the measurement was done repeatedly with the time delay changed. Depending on the timing of applying the DC control voltage signal (f), the output signal of the envelope detecting section 13 changes, and the integrated signal (g) changes at the decision section 14 as a result.

When the integrated values (represented by the integrated signal (g)) are obtained the same number of times as that of repetition in Steps 205 and 206, the decision section 14 determines the maximum value and a time delay associated with the maximum value in Step 207. The distance calculating section 15 subjects the ultrasonic wave propagation velocity to temperature correction if necessary, obtains the propagation time of the ultrasonic wave based on the time delay, and thereby calculates the distance to the object.

According to the present invention, while the resonant frequency of the ultrasonic transducer is changed, a frequency-modulated drive signal is applied or a frequency-modulated ultrasonic wave is received. That is why even if the piezoelectric element of the ultrasonic transducer has a narrow band, the ultrasonic wave can still be transmitted and received in a sufficiently broad range and the frequency-modulated ultrasonic wave can be transmitted and received. Consequently, measurements can be done highly accurately without being easily affected by various fluctuations in the measuring environment including noise and wind.

Also, in the present invention, a narrow-band piezoelectric element is used as the ultrasonic transducer so as to be driven with small power. As a result, a small-sized, easily portable ultrasonic distance measure is realized by using a battery as a power supply, for example.

In addition, since no correlation circuit is used to detect the received wave, the receiver can have a simplified configuration and a less expensive ultrasonic distance measure is realized.

In the preferred embodiment described above, the ultrasonic distance measure includes a propagation time premeasuring section. However, if an approximate distance to the object of measurement is already known or if the range of measurement needs to be limited, then the propagation time premeasuring section can be omitted. In that case, the time delay may be set in advance by the delay section 16 based on either the predefined range or the approximately known distance, and the measurement can be done by performing Step 204 and following processing steps shown in FIG. 14 without calculating any estimated distance.

Also, in the preferred embodiment described above, the transmitting ultrasonic transducer 1 and receiving ultrasonic transducer 2 are used. Alternatively, the ultrasonic wave may be transmitted and received by a single ultrasonic transducer. In that case, a switching section needs to work between the transmitting/receiving ultrasonic transducer and the transmitting section 151 with the transmitting control voltage generating section 152 or the receiving section 154 with the receiving control voltage generating section 153. And the connection between these blocks may be switched synchronously with the transmission or reception.

Furthermore, in the preferred embodiment described above, the driving section generates a chirp signal by modulating a carrier signal having a predetermined frequency with a modulating signal. Alternatively, a pulse signal, of which the pulse width and pulse interval change just like a chirp signal, may also be used.

Also, in the present invention, a narrow-band piezoelectric element is used as the ultrasonic transducer so as to be driven with small power. As a result, a small-sized, easily portable ultrasonic distance measure is realized by using a battery as a power supply, for example.

Besides, since no correlation circuit is used to detect the received wave, the receiver can have a simplified configuration and a less expensive ultrasonic distance measure is realized.

What is more, according to the present invention, an approximate propagation time is calculated first by the propagation time premeasuring section, and therefore, the measurable range can be broadened. In addition, any distance within the measurable range can be measured in a shorter time.

Figure 19:
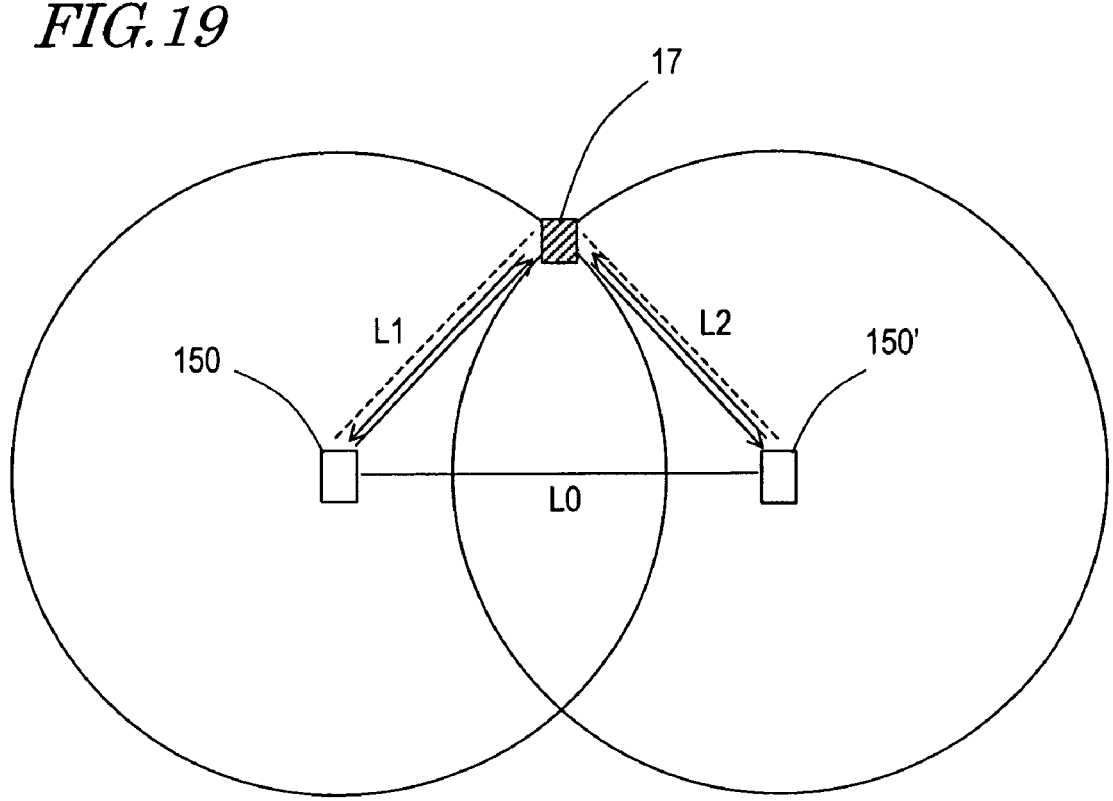
FIG. 19 shows a direction finder that uses ultrasonic distance measures of the present invention.

On top of that, the direction of the object of measurement can be found by using a plurality of ultrasonic distance measures according to the present invention. As shown in FIG. 19, the ultrasonic distance measure 150 and another ultrasonic distance measure 150' are arranged with a predetermined gap L0 provided between them, and the distances to the object of measurement 17 are measured with these ultrasonic distance measures. Supposing the distances from the ultrasonic distance measures 150 and 150' to the object of measurement are identified by L1 and L2, respectively, the object of measurement is located at an intersection between two circles, of which the centers are spaced apart from each other by L0 and of which the radii are equal to L1 and L2, respectively. In this manner, the direction of the object of measurement 17 as viewed from the ultrasonic distance measures 150 and 150' can be found. If measurement is done in a similar procedure by using three or more ultrasonic distance measures, the direction of an object of measurement in a three-dimensional space can also be found.

Embodiment 2

Figure 20:
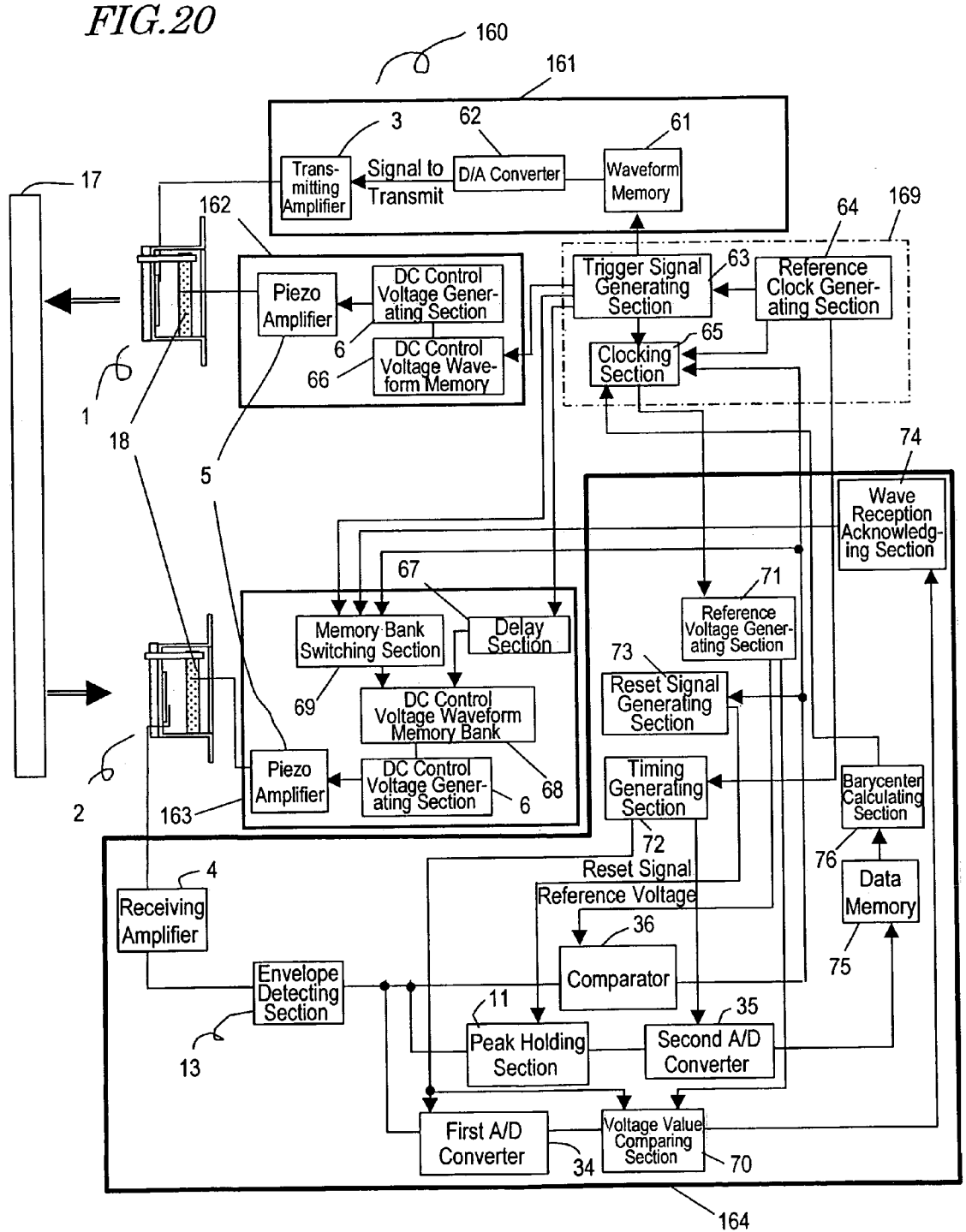
FIG. 20 is a block diagram showing a configuration for a second preferred embodiment of an ultrasonic distance measure according to the present invention.

Hereinafter, a second preferred embodiment of an ultrasonic distance measure according to the present invention will be described. As shown in FIG. 20, the ultrasonic distance measure 160 of this preferred embodiment includes a transmitting ultrasonic transducer 1, a receiving ultrasonic transducer 2, a driving section 161, a transmitting control voltage generating section 162, a receiving control voltage generating section 163 and a receiving section 164. The ultrasonic distance measure 160 further includes a timing section 169 for adjusting control timings of these sections. The timing section 169 includes: a reference clock generating section 64 for generating a clock signal as an overall reference; a trigger signal generating section 63 for sending a trigger signal to the driving section 161, transmitting control voltage generating section 162 and receiving control voltage generating section 163; and a clocking section 65.

As the transmitting and receiving ultrasonic transducers 1 and 2, ultrasonic transducers, of which the resonant or resonance frequencies are changeable, are used as already described for the first preferred embodiment. For example, the ultrasonic transducers 101, 102, 103 described for the first preferred embodiment can be used effectively. In this preferred embodiment, the ultrasonic transducers 101 are used.

The driving section 161 generates a measuring drive signal to drive the transmitting ultrasonic transducer 1 and transmit a measuring ultrasonic wave, and applies the measuring drive signal generated to the transmitting ultrasonic transducer 1. The driving section 161 preferably includes a waveform memory 61 in which the waveform of the measuring drive signal generated in advance is stored, a D/A converter 62, and a transmitting amplifier 3. The waveform memory 61 stores the pre-generated measuring drive signal in digital form. The D/A converter 62 converts the measuring drive signal in digital form into an analog signal and outputs it to the transmitting amplifier 3. In response, the transmitting amplifier 3 amplifies the received signal and then outputs it to the transmitting ultrasonic transducer 1. The timing of sending out the measuring drive signal in digital form from the waveform memory 61 to the D/A converter 62 is set by the trigger signal that has been output from the trigger signal generating section 63 to the waveform memory 61. The trigger signal generating section 63 operates in response to the reference clock signal generated by the reference clock generating section 64.

Figure 21:
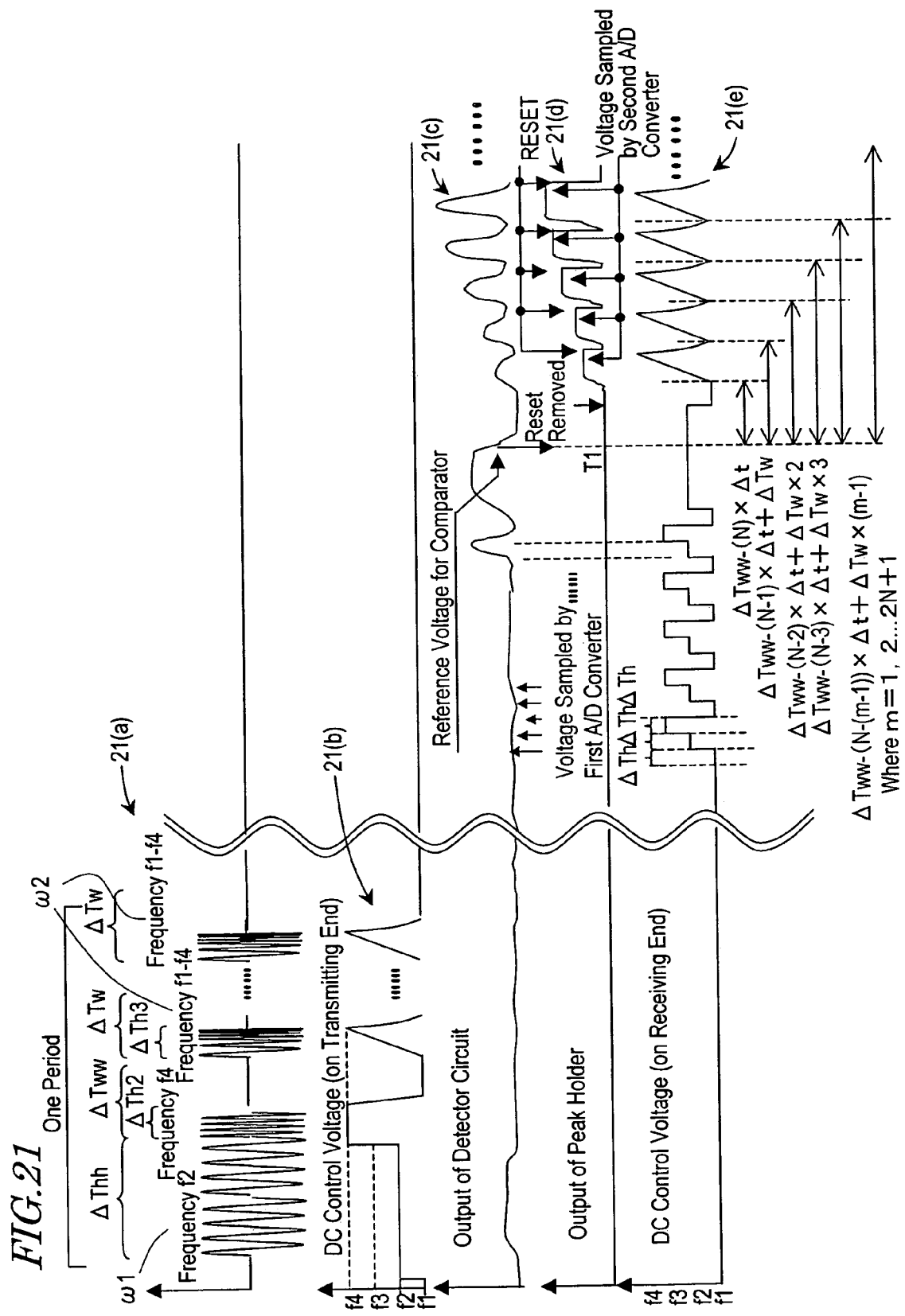
FIG. 21 is a timing diagram showing signals at respective components of the ultrasonic distance measure shown in FIG. 20.
Figure 22:
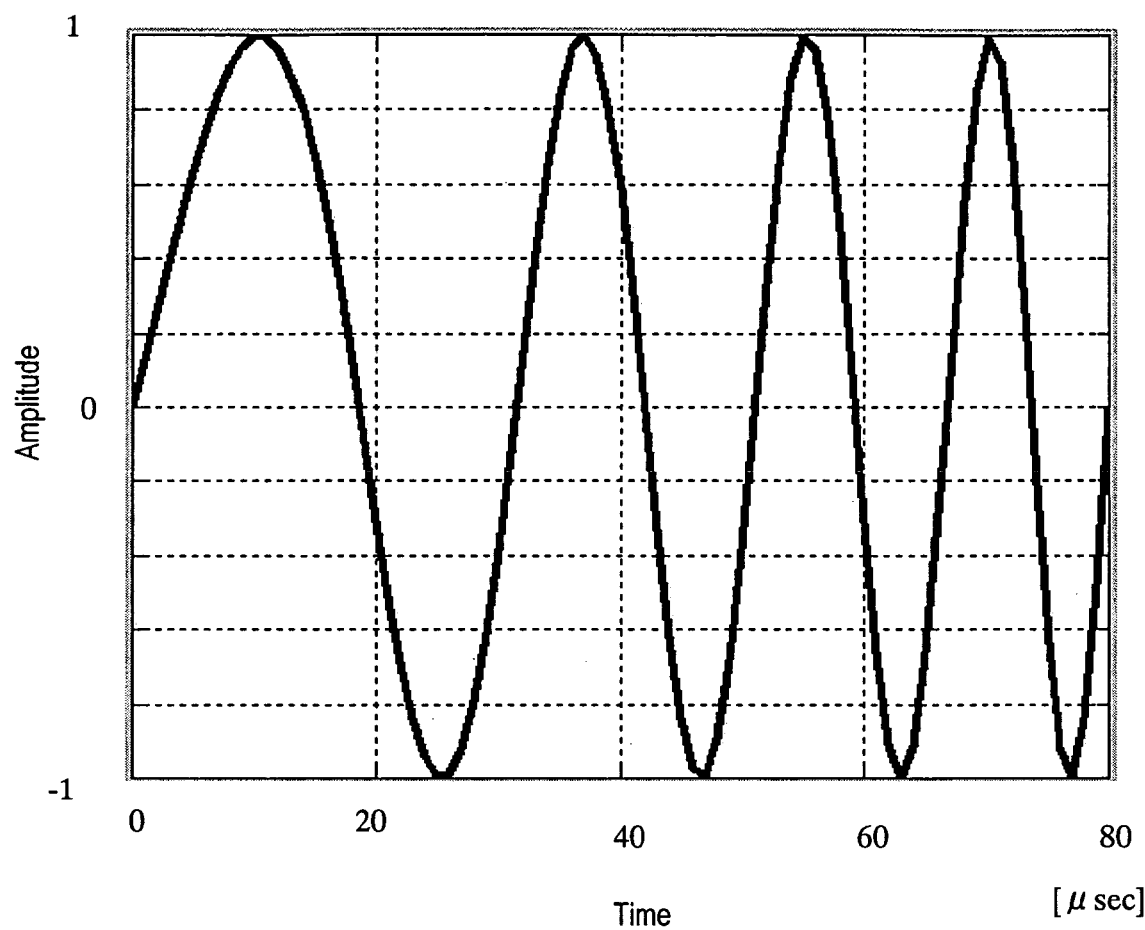
FIG. 22 shows the waveform of the output signal of the transmitting amplifier of the ultrasonic distance measure shown in FIG. 20.

As shown in FIG. 21, the measuring drive signal 21(a) includes a drive signal w1 (corresponding to the "second drive signal") and a plurality of drive signals w2 (corresponding to the "first drive signal"). The drive signal w1 is used to sense that the reflected wave of the ultrasonic wave, transmitted responsive to the measuring drive signal, has reached the receiving ultrasonic transducer 2. Meanwhile, the drive signal w2 is used to set a reference time for measuring. The drive signal W1 is a sine wave, of which the frequency switches halfway. More specifically, after having maintained a frequency f2 (corresponding to the "first frequency") during a period $\Delta Thh$, the drive signal W1 switches its frequency from f2 into f4 and then maintains the frequency f4 (corresponding to the "second frequency") during $\Delta Th2$. The drive signals w2 are output during a period $\Delta Th3$. In the meantime, the frequency of the drive signal w2 changes linearly from f1 to f4. The drive signal w2 has an iterative period of $\Delta Tw$, which is repeated 2N+1 times. The first drive signal w2 is output when the amount of time ($\Delta Thh+\Delta Tww$) has passed since the drive signal W1 started to be output. The frequencies f1 through f4 satisfy the inequality f1<f2<f3<f4. For example, f1=20 kHz, f2=40 kHz, f3=60 kHz and f4=80 kHz. If $\Delta Th3$ is 80 μs, a waveform of which the frequency sweeps linearly from 20 kHz to 80 kHz is as shown in FIG. 22.

The transmitting control voltage generating section 162 generates a DC control voltage that changes the resonant or resonance frequency of the transmitting ultrasonic transducer 1. For that purpose, the transmitting control voltage generating section 162 includes a DC control voltage generating section 6, a DC control voltage waveform memory 66 and a piezo amplifier 5. In the DC control voltage waveform memory 66, a control voltage waveform having a profile that makes the resonant or resonance frequency of the transmitting ultrasonic transducer 1 change substantially synchronously with the frequency of the measuring drive signal is stored. The DC control voltage generating section 6 reads the DC control voltage waveform in digital form from the DC control voltage waveform memory 66, converts the digital form into an analog form, and also shifts its range to a best range for the piezo amplifier 5. The piezo amplifier 5 amplifies the DC control voltage and applies the amplified control voltage to the actuator 18 of the transmitting ultrasonic transducer 1. When the DC control voltage is applied to the actuator 18, the transmitting ultrasonic transducer 1 transmits an ultrasonic wave in response to the drive signal while changing its resonant frequency.

As represented by the signal 21(*b*) in FIG. 21, while the drive signal W1 is being output, the DC control voltage maintains a value that drives the actuator 18 such that the resonant or resonance frequency of the transmitting ultrasonic transducer 1 becomes equal to the frequency f2 during the period ΔThh and then maintains a value that drives the actuator 18 such that the resonant or resonance frequency becomes equal to f4 during ΔTh2. Thereafter, the DC control voltage has values that drive the actuator 18 such that the resonant or resonance frequency of the transmitting ultrasonic transducer 1 changes from f1 through f4 synchronously with the frequency variation of the drive signal w2.

The operations of the driving section 161 and the transmitting control voltage generating section 162 are controlled by the trigger signal generating section 63. More specifically, in response to the trigger signal generated by the trigger signal generating section 63, the measuring drive signal in the digital form is transferred from the waveform memory 61 to the D/A converter 62, amplified by the transmitting amplifier 3 and then drives the transmitting ultrasonic transducer 1. In this case, the data representing the DC control voltage waveform is read out from the DC control voltage waveform memory 66 in response to the trigger signal such that the frequency of the wave to be transmitted agrees with the resonant frequency of the transmitting ultrasonic transducer 1. Then, the piezo amplifier 5 applies the DC control voltage to the actuator 18. Also, in the trigger signal generating section 63, the clocking section 65 starts counting so as to begin clocking when the amount of time ΔThh has passed since the transmission start signal rose.

The ultrasonic wave that has been transmitted from the transmitting ultrasonic transducer 1 travels toward, and then is reflected by, the object of measurement 17. Thereafter, the ultrasonic reflected wave reaches the receiving ultrasonic transducer 2 and then is converted by the receiving ultrasonic transducer 2 into an electrical signal.

The receiving control voltage generating section 163 includes a piezo amplifier 5, a DC control voltage generating section 6, a memory bank switching section 69 and a DC control voltage waveform memory bank 68, and generates a DC control voltage to change the resonant or resonance frequency of the receiving ultrasonic transducer 2. The piezo amplifier 5 and DC control voltage generating section 6 have similar configurations to the counterparts of the transmitting control voltage generating section 162. On the receiving end, however, the DC control voltage generating section 6 generates the DC control voltage in response to the output signal of a delay section 67, not the trigger signal supplied from the trigger signal generating section 63. The DC control voltage waveform memory bank 68 stores first, second and third DC control voltage waveforms, which are switched by the memory bank switching section 69. These three types of DC control voltage waveforms are shown in FIGS. 23A, 23B and 23C, respectively.

Figure 23A:
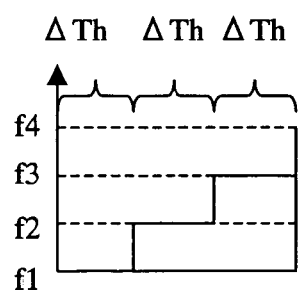
FIG. 23A shows the waveform of an exemplary DC control voltage applied to the actuator of a receiving ultrasonic transducer.
Figure 23B:
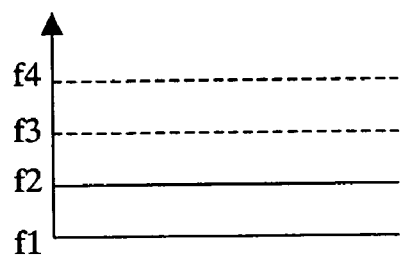
FIG. 23B shows the waveform of another exemplary DC control voltage applied to the actuator of the receiving ultrasonic transducer.
Figure 23C:
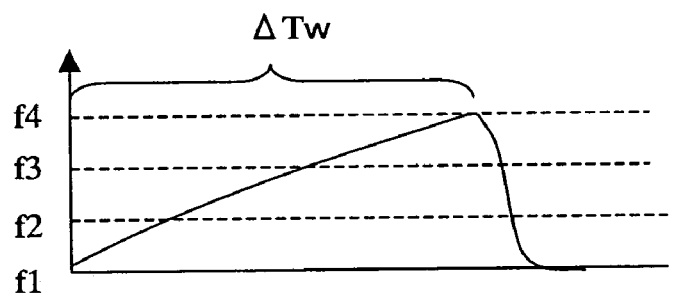
FIG. 23C shows the waveform of another exemplary DC control voltage applied to the actuator of the receiving ultrasonic transducer.

As shown in FIG. 23A, the first waveform is supposed to have amplitude that drives the actuator 18 such that the resonant frequency of the receiving ultrasonic transducer 2 changes from f1 into f2 and then f3 every time ΔTh passes. And the first waveform is supposed to be stored in Bank No. 1 of the DC control voltage waveform memory bank 68. The first waveform is used to see if the wave reflected from the object of measurement has reached the receiving ultrasonic transducer 2. As shown in FIG. 23B, the second waveform has constant amplitude that drives the actuator 18 such that the resonant frequency of the receiving ultrasonic transducer 2 becomes equal to f2. This waveform is stored in Bank No. 2 of the DC control voltage waveform memory bank 68. The second waveform (i.e., second control voltage) is used to detect when the frequency changes in the ultrasonic reflected wave that was transmitted in response to the drive signal w1. As shown in FIG. 23C, the third waveform is defined such that the resonant frequency of the receiving ultrasonic transducer 2 sweeps linearly from f1 through f4 in a period of time ΔTh3. This waveform is stored in Bank No. 3 of the DC control voltage waveform memory bank 68. The third waveform (i.e., the first control voltage) is used to measure the propagation time of the ultrasonic wave accurately.

The receiving section 164 includes a receiving amplifier 4, an envelope detecting section 13, a comparator 36, a peak holding section 11, a first A/D converter 34, a second A/D converter 35, a voltage value comparing section 70, a reference voltage generating section 71, a timing generating section 72, a reset signal generating section 73, a wave reception acknowledging section 74, a data memory 75 and a barycenter calculating section 76.

As described above, the measuring drive signal includes a drive signal w1 and a plurality of drive signals w2. If the receiving section 164 has received an ultrasonic reflected wave that was transmitted in response to the drive signal w1, then the envelope detecting section 13, first A/D converter 34, voltage value comparing section 70 and wave reception acknowledging section 74 are used to see if the wave reflected from the object of measurement 17 has arrived. Also, by using the comparator 36, a reference time is set in measuring the propagation time of the ultrasonic wave accurately in response to the drive signals w2. On the other hand, if a plurality of ultrasonic reflected waves have been received in response to the drive signals w2, then the peak holding section 11, second A/D converter 35, data memory 75 and barycenter calculating section 76 are used to obtain an accurate propagation time of each ultrasonic wave.

Figure 24A:
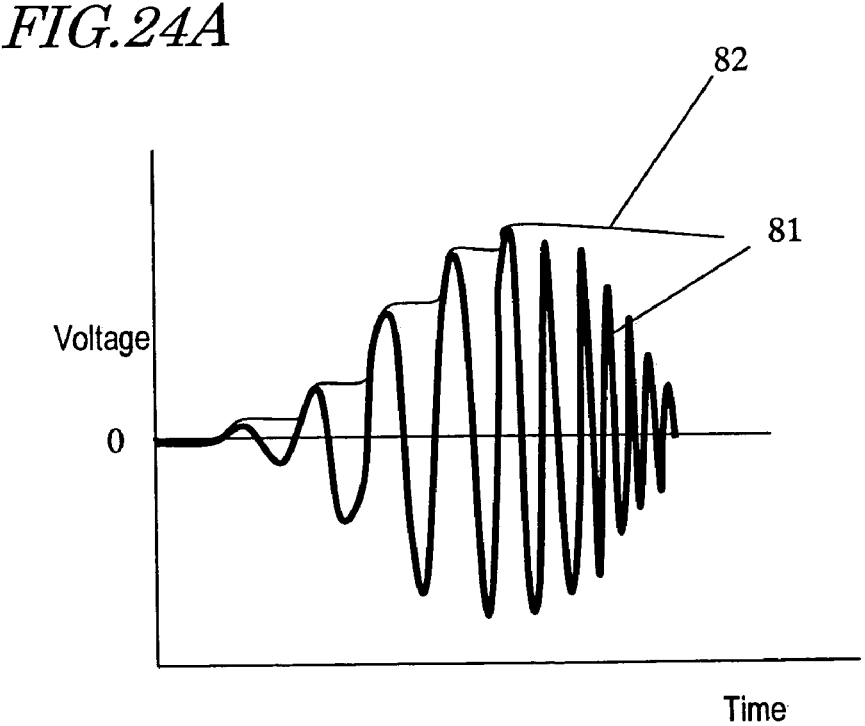
FIG. 24A shows a received signal and its peak holding signal detected at the receiving section of the ultrasonic distance measure shown in FIG. 20.
Figure 24B:
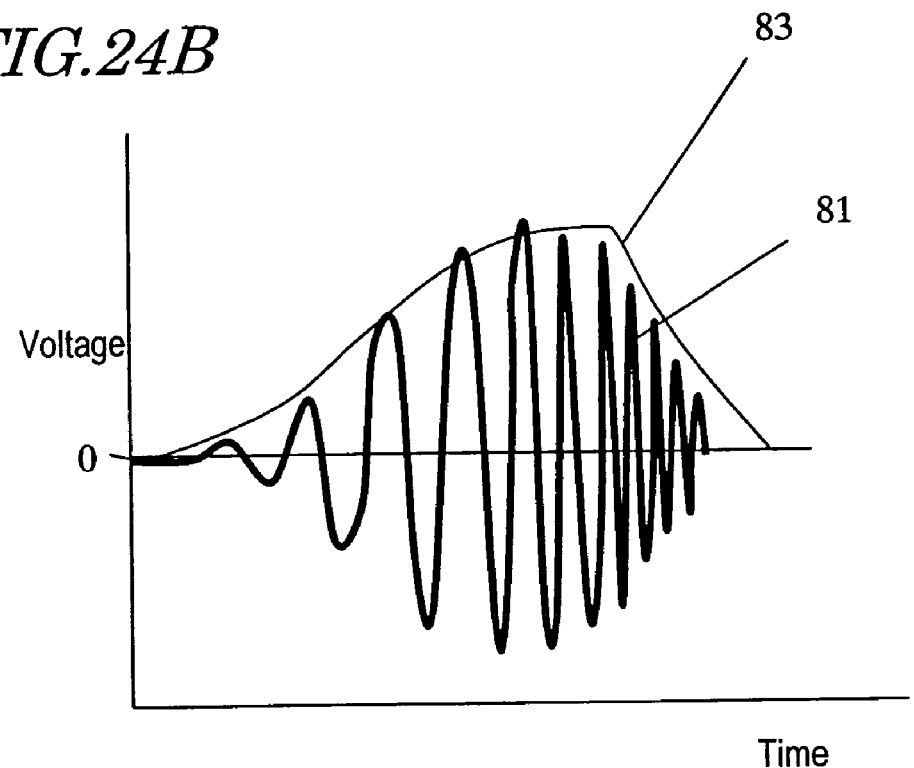
FIG. 24B shows a received signal and its envelope detection signal detected at the receiving section of the ultrasonic distance measure shown in FIG. 20.

The receiving amplifier 4 amplifies the received signal that has been converted by the receiving ultrasonic transducer 2. The envelope detecting section 13 generates and outputs an envelope signal of the received signal. The peak holding section 11 holds the maximum amplitude of the received signal until a reset signal is input thereto. FIG. 24A shows the output signal 82 of the peak holding section 11 in response to the received signal 81, while FIG. 24B shows the output signal 83 of the envelope detecting section 13 in response to the received signal 81.

The comparator 36 receives the envelope signal from the envelope detecting section 13 and outputs "High" if the envelope signal is higher than the reference voltage and "Low" otherwise. The reference voltage is generated by the reference voltage generating section 71 by reference to the counter value of the clocking section 65. The reference voltage is generated so as to decrease proportionally to the counter value of the clocking section 65.

The second A/D converter 35 converts the voltage value of the peak holding section 11 into a digital value. It should be noted that the reset signal for the peak holding section 11 and the clock signal for the second A/D converter 35 are generated by the timing generating section 72 in response to the reference clock signal generated by the reference clock generating section 64. The first A/D converter 34 converts the output signal of the envelope detecting section 13 into a digital value. To sense a variation in the output signal of the first A/D converter 34, the voltage value comparing section 70 compares the output signal value of the first A/D converter 34 with the previous and next values at predetermined timing. A sampling clock signal is generated for the first A/D converter 34 by the timing generating section 72, too. The comparison is also made by the voltage value comparing section 70 in response to the clock signal supplied from the timing generating section 72.

The wave reception acknowledging section 74 determines, by the output of the voltage value comparing section 70, whether the reflected wave has reached or not. The data memory 75 stores the output of the second A/D converter 35. By reference to the data stored in the data memory 75, the barycenter calculating section 76 locates the barycenter of the output values of the second A/D converter 35, representing the intensity of the received signal, on the delay time axis.

Hereinafter, it will be described with reference to FIGS. 20 and 21 how this ultrasonic distance measure 160 works in measuring the distance. As described above, the transmitting section 161 generates the measuring drive signal 21(a) and the transmitting ultrasonic transducer 1 transmits a measuring ultrasonic wave. In this case, the actuator 18 of the transmitting ultrasonic transducer 1 is driven with the signal 21(b) generated by the transmitting control voltage generating section 162, thereby changing the resonant frequency of the transmitting ultrasonic transducer 1.

As represented by the signal 21(c) in FIG. 21, while the ultrasonic distance measure 160 is in standby state or when the ultrasonic distance measure 160 begins measuring, the output of the receiving control voltage generating section 163 is zero. At this point in time, no voltage is applied to the actuator 18 of the receiving ultrasonic transducer 2 and the resonant frequency of the receiving ultrasonic transducer 2 is f1. Thereafter, the waveform in Bank No. 1 is output to change the resonant frequency of the receiving ultrasonic transducer 2 from f1 into f2 and then f3 every time ΔTh passes. Furthermore, the A/D converter 34 measures the output voltage of the detector circuit every time a sampling period ΔTh passes. The measuring timing is defined just before the resonant frequency of the ultrasonic transducer 2 changes. The timing of outputting the waveform from Bank No. 2 depends on the distance to be measured by the ultrasonic distance measure 160. Specifically, if the ultrasonic distance measure 160 is going to measure a short distance, the waveform in Bank No. 1 may be output when or right after the ultrasonic wave has been transmitted. Also, if the ultrasonic wave transmitted from the transmitting ultrasonic transducer 1 could reach the receiving ultrasonic transducer 2 directly, then the waveform in Bank No. 1 should preferably be output after the ultrasonic wave has been transmitted.

Considering the time constant of the envelope detecting section 13 and the response of the actuator 18, the length of the sampling period ΔTh preferably corresponds to at least five wavelengths of the ultrasonic wave for measuring. For example, if f2 is 40 kHz, then ΔTh is preferably at least equal to 125 μs (=25 μs×5). In that case, the first A/D converter 34 has a sample rate of 8 kHz. Also, the period of time ΔThh for which the frequency f2 is maintained in response to the drive signal w1 is preferably at least four times as long as ΔTh. To set a reference time with the drive signal w1 in measuring the propagation time of the ultrasonic wave accurately using the drive signals w2, the period ΔThh is preferably about 2 ms when f2 is 40 kHz.

By getting the reflected wave received by the receiving ultrasonic transducer 2, the receiving amplifier 4 generates a received signal and the envelope detecting section 13 generates an envelope detection signal, which is converted by the first A/D converter 34 into a digital value. In every sampling period, the voltage value comparing section 70 compares a value when the resonant frequency of the receiving ultrasonic transducer 2 is equal to the frequency f2 with the previous and next values. And if the ratio of the former value to the previous or next value is equal to or greater than some reference value, then the wave reflected from the obstacle 17 is regarded as having reached. This is because if the resonant frequency of the receiving ultrasonic transducer 2 agrees with the frequency of the reflected wave, then the reflected wave should be received at a high intensity. This reference value is determined based on the value of the reference voltage generating section 71. Also, the decision is made by the wave reception acknowledging section 74. The smaller the reference voltage value, the longer the distance to the object of measurement and the greater the degree of attenuation of the reflected wave. In that case, the received signal has also attenuated accordingly. That is why the reference value is set low then.

If not the wave reflected from the object of measurement 17 but white noise, for example, has been received, then the voltage value of the first A/D converter 34 becomes constant irrespective of the resonant frequency of the receiving ultrasonic transducer 2. On the other hand, if pink noise has been received, then the voltage value of the first A/D converter 34 increases as the resonant frequency of the receiving ultrasonic transducer 2 decreases. That is why the chances to take the noise for a measuring ultrasonic wave by mistake are very low.

If the wave reception acknowledging section 74 has acknowledged the reception of the reflected wave, then an approximate propagation time needs to be detected. The detected time will be used as a reference time for figuring out a more accurate propagation time. On acknowledging the reception of the reflected wave, the wave reception acknowledging section 74 signals the memory bank switching section 69 to select Bank No. 2 in the DC control voltage waveform memory bank 68. As a result, a DC control voltage having the waveform stored in Bank No. 2 is applied to the actuator 18 of the receiving ultrasonic transducer 2 and the resonant frequency of the receiving ultrasonic transducer 2 is kept equal to f2. If the frequency of the received signal switches from f2 into f4, then the intensity of the received signal decreases steeply due to the disagreement of frequencies and the output of the envelope detecting section 13 decreases. The comparator 36 compares the output of the envelope detecting section 13 with the reference voltage, and switches the output from High into Low when finding the output of the envelope detecting section lower than the reference voltage. The clocking section 65 records the time T1 when the output of the comparator 36 changes.

A reference voltage value (of −3 dB, for example) for the comparator 36 is supposed to be smaller than the output value of the envelope detecting section 13 when the first A/D converter 34 acknowledges the reception of the reflected wave being detected. By setting the reference voltage for the comparator 36 based on the actually detected intensity of the reflected and received wave, measurements can be done accurately even if the received signal has attenuated according to a propagation distance or environment.

Once the time T1 has been recorded in the clocking section 65, the peak holding section 11 is not reset anymore. The reset signal is generated by the reset signal generating section 73. At the same time, the reset signal generating section 73 signals the memory bank switching section 69 to select Bank No. 3 in the DC control voltage waveform memory bank 68.

As represented by the signal 21(a) in FIG. 21, the drive signal w2 is repeatedly output a number of times at an interval of ΔTw. Accordingly, when the interval ΔTw has passed since the time T1, the reflected wave reaches the receiving ultrasonic transducer 2 and a received signal is detected. On the other hand, the DC control voltage for driving the actuator 18 of the receiving ultrasonic transducer 2 is output every time a different amount of time delay, which changes by Δt with respect to the time when the ultrasonic reflected wave reaches in response to each drive signal w2, has passed. As in the first preferred embodiment described above, this time delay is added backward on the time axis to the timing of receiving the reflected wave. If the drive signal w2 should be output (2N+1) times, then the time delays will be −N×Δt, −(N−1)×Δt, −(N−2)×Δt . . . , Δt, 1×Δt, 2×Δt, . . . and N×Δt.

The arrival times of the reflected wave will be ΔTww, ΔTww+ΔTw, ΔTww+2×ΔTw, ΔTww+3×ΔTw . . . , and ΔTww+2N×ΔTw with respect to the time T1. Thus, the timings of applying the DC control voltage for driving the actuator 18 of the receiving ultrasonic transducer 2 will be ΔTww−(N−m)×Δt+ΔTw×(m−1) with respect to the time T1, where m=1, 2, . . . , and 2N+1.

As represented by the signal 21(e) in FIG. 21, in detecting the ultrasonic reflected wave that was transmitted in response to the drive signal w2 applied for the first time, the piezo amplifier 5 applies the DC control voltage to the actuator 18 of the receiving ultrasonic transducer 2 when the amount of time ΔTww−(N)×Δt has passed since the time T1. Thereafter, when the amount of time (ΔTww−(N−1)×Δt+ ΔTw−α) has passed since the time T1, the output signal of the peak holding section 11 is read by the second A/D converter 35 and stored in the data memory 75. When the signal has been read by the second A/D converter 35, the peak holding section 11 will be reset.

In detecting the ultrasonic reflected wave that was transmitted in response to the drive signal w2 applied next, the piezo amplifier 5 applies the DC control voltage to the actuator 18 of the receiving ultrasonic transducer 2 when the amount of time ΔTww−(N−1)×Δt+ΔTw has passed since the time T1. Thereafter, when the amount of time (ΔTww−(N− 2)×Δt+2×ΔTw−α) has passed since the time T1, the output signal of the peak holding section 11 is read by the second A/D converter 35 and stored in the data memory 75. When the signal has been read by the second A/D converter 35, the peak holding section 11 will be reset.

In this manner, a series of operations consisting of:
(1) applying the DC control voltage to the actuator 18 of the receiving ultrasonic transducer 2 after the amount of time (ΔTww−(N−(m−1))×Δt+ΔTw×(m−1)) has passed since the time T1;
(2) getting the output voltage value of the peak holding section 11 read by the second A/D converter 35 and stored in the data memory 75 when the amount of time (ΔTww−(N−m)×Δt+ΔTw×m−a) has passed since the time T1; and
(3) resetting the peak holding section 11 when the read operation is done by the second A/D converter 35 are repeatedly carried out until m reaches 2N+1.

After these repetitive measurements have been done, the barycenter calculating section 76 reads out 2N+1 data items from the data memory 75, and arranges those items at the intervals of Δt, thereby calculating the barycenter $\Delta t_G$ of the output values of the second A/D converter 35 on the axis of time delay. Supposing the output value of the second A/D converter upon the reception of the ultrasonic reflected wave that was transmitted in response to each drive signal w2 is identified by $A_m$, the barycenter $\Delta t_G$ is given by:

$$\Delta t_G = \frac{\sum_{m=1}^{m=2N+1} A_m \times (m-1) \times \Delta t}{\sum_{m=1}^{m=2N+1} A_m} \quad \text{[Equation 1]}$$

Figure 25:
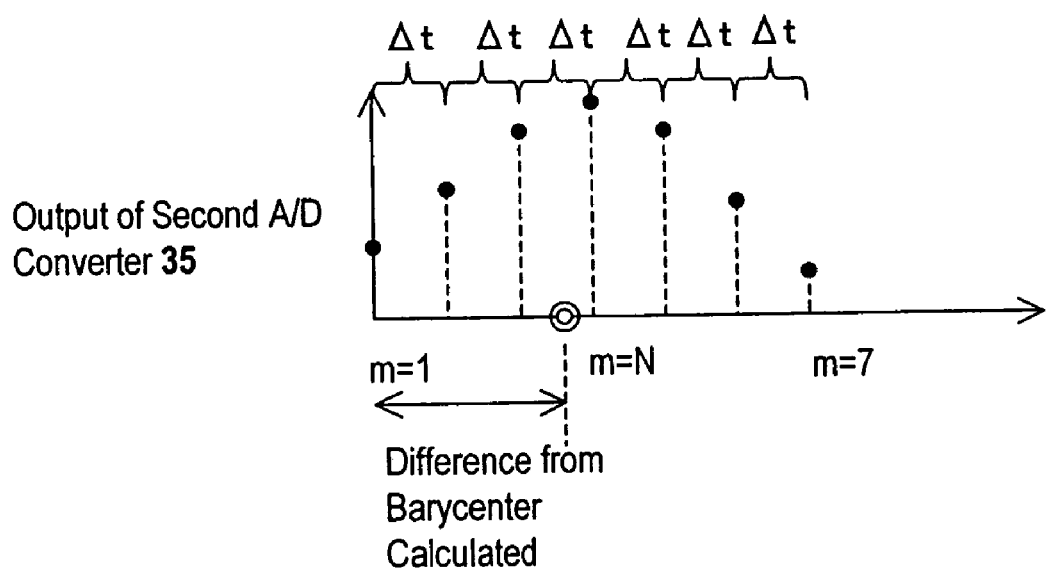
FIG. 25 is a graph showing the distribution of output values of a second A/D converter.

For example, when N=3, the graph shown in FIG. 25 can be obtained.

The closer the timings of frequency variation of the reflected wave received and the timings of variation in the resonant frequency of the receiving ultrasonic transducer 2, the greater the output value of the second A/D converter 35. And the less close those timings are, the smaller the output value of the second A/D converter 35 becomes. That is why by calculating the barycenter $\Delta t_G$ of the output values of the second A/D converter 35 on the axis of time delay, the time delay can be interpolated even if the timings of frequency variation of the reflected wave received and the timings of variation in the resonant frequency of the receiving ultrasonic transducer 2 do not completely agree with each other. That is to say, at the barycenter $\Delta t_G$ on the axis of time delay, the output value of the second A/D converter 35, representing the intensity of the received signal, becomes maximum. Consequently, the barycenter $\Delta t_G$ represents a time delay in which the timings of frequency variation of the reflected wave received and the timings of variation in the resonant frequency of the receiving ultrasonic transducer 2 agree most closely with each other.

N is preferably at least equal to three. The smaller N, the larger Δt should be. Conversely, the larger N, the smaller Δt can be. Also, if ΔTw is 100 μs, for example, the second A/D converter 35 has a sampling frequency of 10 kHz. The resolution of the second A/D converter 35 is preferably at least equal to 10 bits because it affects the precision of the barycenter calculation.

The propagation time is obtained by subtracting N×Δt from the barycenter value $\Delta t_G$ of the received signal intensities and by adding T1 to the remainder. If the propagation time thus obtained is multiplied by the sonic velocity, then a round trip distance to the object of measurement 17 is known. And by dividing this distance by two, the distance to the object of measurement 17 can be obtained. As in the first preferred embodiment, temperature correction is preferably made.

In the ultrasonic distance measure of this preferred embodiment, while the resonant frequency of the ultrasonic transducer is changed, a frequency-modulated drive signal is applied or a frequency-modulated ultrasonic wave is received as in the first preferred embodiment described above. That is why even if the piezoelectric element of the ultrasonic transducer has a narrow band, the ultrasonic wave can still be transmitted and received in a sufficiently broad range and the frequency-modulated ultrasonic wave can be transmitted and received. Consequently, measurements can be done highly accurately without being easily affected by various fluctuations in the measuring environment including noise and wind. In particular, even if the received signal has attenuated according to the propagation distance or environment, measurements can still be done accurately by improving the method of detecting the wave reflected by the object of measurement.

Figure 26:
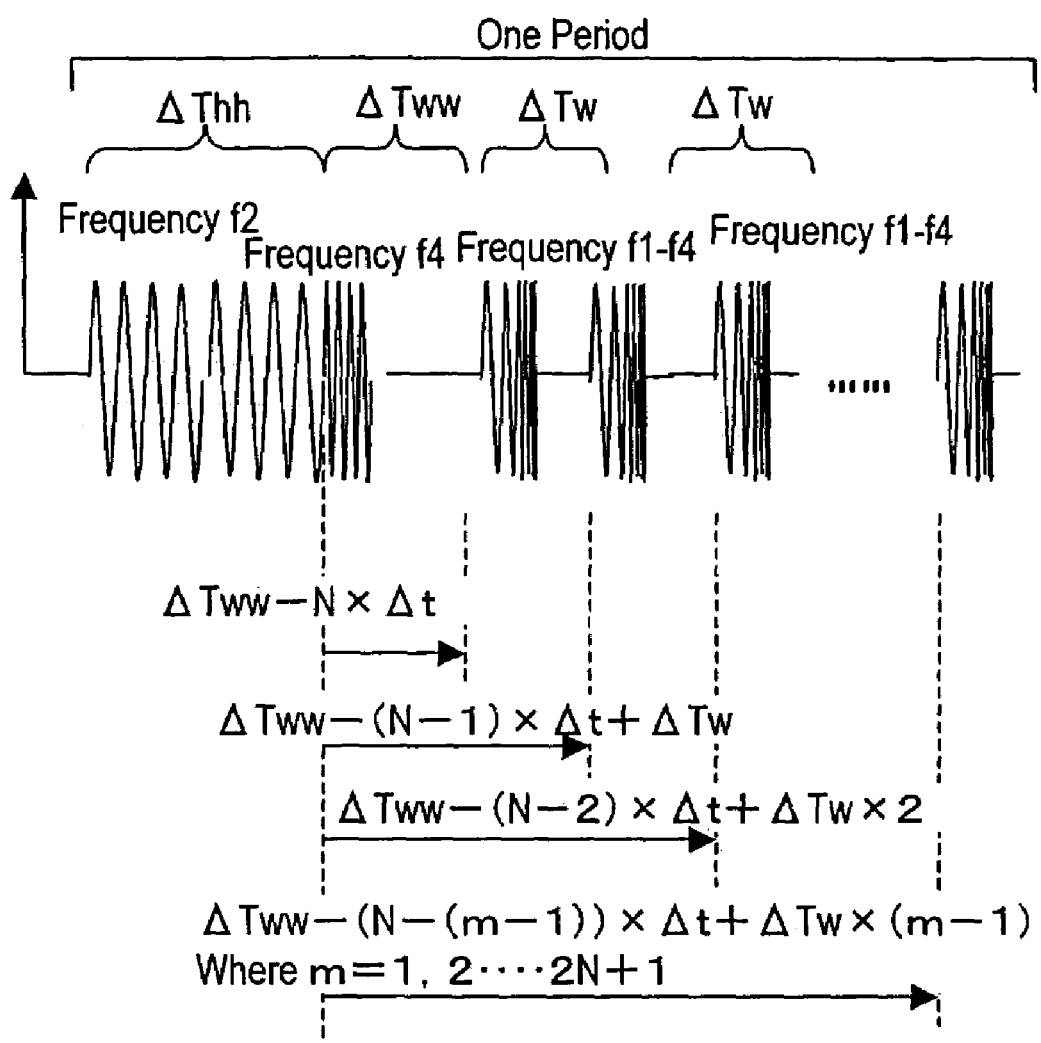
FIG. 26 shows another exemplary waveform of the output signal of the transmitting amplifier of the ultrasonic distance measure shown in FIG. 20.

In the preferred embodiment described above, the frequency-modulated ultrasonic wave is transmitted a number of times at regular intervals and the time delay for applying the DC control voltage, which represents the timing of changing the resonant frequency of the receiving ultrasonic transducer, is changed by $\Delta t$ every time. That is to say, the frequency-modulated ultrasonic wave is transmitted at the same intervals, while the time delay for applying the DC control voltage to the receiving ultrasonic transducer is changed. However, the propagation time of the ultrasonic wave can also be calculated accurately as long as one of the time interval and time delay is constant and the other is variable. Accordingly, even if the frequency-modulated drive signal is applied with the timing of application shifted by $\Delta t$ each time and if the time delay for applying the DC control voltage to the receiving ultrasonic transducer is kept constant as shown in FIG. 26, the propagation time of the ultrasonic wave can also be calculated accurately.

In the ultrasonic distance measure of the second preferred embodiment, the driving section generates a chirp signal by modulating a carrier signal having a predetermined frequency with a modulating signal. Alternatively, a pulse signal, of which the pulse width and pulse interval change just like a chirp signal, may also be used as described for the first preferred embodiment. As also described for the first preferred embodiment, a direction finder for finding the direction of an object of measurement may be realized by using a plurality of ultrasonic distance measures according to this preferred embodiment.

The present invention can be implemented as a distance measure for measuring the distance to an object of measurement in various fields of applications. Also, since an ultrasonic wave is used, the present invention can be used effectively in calculating the distance to a powder, a specular reflector, a transparent body or any other object of measurement of which the distance is hard to measure with a laser beam. In addition, having the advantageous features described above, the ultrasonic distance measure of the present invention can also measure the distance accurately enough even in a rather noisy environment, in an atmosphere fluctuating due to wind in the air, for example, and in any other environment that is difficult for a conventional ultrasonic distance measure to cope with. These features allow the user of the ultrasonic distance measure of the present invention to use it as an environment sensor for robots.

Furthermore, the ultrasonic distance measure of the present invention can be used effectively as an ultrasonic flowmeter as not being affected by the environment easily. In that case, the transmitting ultrasonic transducer and receiving ultrasonic transducer are arranged so as to face each other with a channel, through which a fluid under measurement flows, interposed between them such that the ultrasonic wave propagation path formed between the transmitting and receiving ultrasonic transducers is not perpendicular to the fluid flowing direction. The distance between the transmitting and receiving ultrasonic transducers and the propagation velocity of the ultrasonic wave when the fluid stands still should be calculated in advance. Then, the ultrasonic wave is directly transmitted from the transmitting ultrasonic transducer to the receiving ultrasonic transducer and the propagation time is estimated in the procedure described above. The estimated propagation time is affected by the flow of the fluid to be determined by the propagation path of the ultrasonic wave and the flowing direction of the fluid. Thus, the flow velocity and flow rate of the fluid can be obtained based on the propagation time and propagation distance measured and the propagation velocity of the ultrasonic wave when the fluid is standing still.

An ultrasonic distance measure according to the present invention can accurately determine the distance to an object of measurement without being easily affected by noise or fluctuations in the surrounding medium, and can be used in various types of distance measures. The ultrasonic distance measure may also be used as an environment sensor for robots, a flowmeter and a direction finder, for example.

Also, an ultrasonic transducer according to the present invention can be used effectively in various ultrasonic devices that should produce vibrations in a broad range. The ultrasonic transducer can be driven with low power, and contributes to making an easily portable ultrasonic device.

This application is based on Japanese Patent Application No. 2004-133303 filed Apr. 28, 2004, the entire contents of which are hereby incorporated by reference that fall within the true spirit and scope of the invention.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention.

What is claimed is:

1. An ultrasonic distance measure comprising:
   a transmitting ultrasonic transducer and a receiving ultrasonic transducer, of which the resonant or resonance frequencies are changeable;
   a driving section, which generates a frequency-modulated drive signal to drive the transmitting ultrasonic transducer and transmit an ultrasonic wave;
   a transmitting control voltage generating section for generating a control voltage to change the resonant or resonance frequency of the transmitting ultrasonic transducer and applying the control voltage to the transmitting ultrasonic transducer that is going to transmit the ultrasonic wave;
   a receiving control voltage generating section for generating a control voltage to change the resonant or resonance frequency of the receiving ultrasonic transducer and applying the control voltage to the receiving ultrasonic transducer when a controllable amount of time delay has passed since the drive signal was generated; and
   a receiving section for sensing the intensity of a signal received as the ultrasonic wave at the receiving ultrasonic transducer,
   wherein the ultrasonic wave is transmitted from the transmitting ultrasonic transducer toward an object of measurement a number of times, reflected, and then received at the receiving ultrasonic transducer with the time delay changed every time, and wherein the ultrasonic distance measure calculates propagation time of the ultrasonic wave based on the time delay that makes the receiving section receive the ultrasonic wave as a signal with the highest intensity, and measures a distance to the object of measurement based on the propagation time.

2. The ultrasonic distance measure of claim 1, further comprising a timing section for generating and outputting a trigger signal that activates the driving section, the transmitting control voltage generating section and the receiving control voltage generating section at predetermined timings,
wherein the receiving control voltage generating section includes a delay section for producing time delays of different lengths at regular time intervals every time the delay section receives the trigger signal.

3. The ultrasonic distance measure of claim 2, further comprising a propagation time premeasuring section, which receives the trigger signal from the timing section and measures how much time has passed after the trigger signal was received and before the signal received at the receiving ultrasonic transducer reaches a predetermined level,
wherein the receiving control voltage generating section produces the time delays based on the amount of time measured by the premeasuring section and responsive to the trigger signal supplied from the timing section.

4. The ultrasonic distance measure of claim 1, wherein the receiving control voltage generating section and the transmitting control voltage generating section generate control voltages that change the resonant or resonance frequencies of the receiving and transmitting ultrasonic transducers substantially in sync with the frequency modulation of the drive signal.

5. The ultrasonic distance measure of claim 1, wherein the drive signal is a chirp signal.

6. The ultrasonic distance measure of claim 1, wherein the drive signal is a pulse signal.

7. The ultrasonic distance measure of claim 1, further comprising a thermometer for measuring an environmental temperature around the object of measurement,
wherein the ultrasonic distance measure corrects propagation velocity of the ultrasonic wave according to the environmental temperature measured and calculates the distance to the object of measurement based on the propagation velocity corrected.

8. The ultrasonic distance measure of claim 1, wherein each of the transmitting and receiving ultrasonic transducers includes a diaphragm, a piezoelectric transducer provided for the diaphragm, and an actuator for shrinking or stretching the diaphragm in response to either the control voltage or the first control voltage.

9. The ultrasonic distance measure of claim 1, wherein each of the transmitting and receiving ultrasonic transducers includes a resonator, a piezoelectric transducer provided for the resonator, and an actuator for changing the resonance frequency of the resonator in response to either the control voltage or the first control voltage.

10. The ultrasonic distance measure of claim 1, wherein each of the transmitting and receiving ultrasonic transducers includes a first acoustic matching layer, a piezoelectric transducer, a second acoustic matching layer provided between the first acoustic matching layer and the piezoelectric transducer, and an actuator for increasing or decreasing the thickness of the second acoustic matching layer in response to either the control voltage or the first control voltage.

11. The ultrasonic distance measure of claim 10, wherein the second acoustic matching layer is a liquid.

12. A direction finder comprising a plurality of ultrasonic distance measures of claim 1 and finding the direction of the object of measurement based on the distances to the object of measurement as measured by the ultrasonic distance measures.

13. A flowmeter comprising the ultrasonic distance measure of claim 1, wherein the transmitting and receiving ultrasonic transducers of the ultrasonic distance measure are arranged so as to face each other with the channel of a fluid interposed and wherein the flowmeter calculates the flow velocity and flow rate of the fluid based on the propagation time of the ultrasonic wave.

14. An ultrasonic distance measure comprising:
a transmitting ultrasonic transducer and a receiving ultrasonic transducer, of which the resonant or resonance frequencies are changeable;
a driving section, which generates a measuring drive signal to drive the transmitting ultrasonic transducer and transmit a measuring ultrasonic wave, the measuring drive signal including a first drive signal that is frequency-modulated and generated a number of times at a predetermined time interval;
a transmitting control voltage generating section for generating a first control voltage to change the resonant or resonance frequency of the transmitting ultrasonic transducer and applying the control voltage to the transmitting ultrasonic transducer that is going to transmit the ultrasonic wave;
a receiving control voltage generating section for generating the first control voltage to change the resonant or resonance frequency of the receiving ultrasonic transducer and applying the first control voltage to the receiving ultrasonic transducer when a predetermined time delay has passed since the first drive signal was generated each time; and
a receiving section for sensing the intensity of a signal received as the ultrasonic wave at the receiving ultrasonic transducer,
wherein the ultrasonic wave is transmitted from the transmitting ultrasonic transducer toward an object of measurement a number of times in response to the first drive signal with one of the time interval and time delay fixed and the other changed, reflected as a first reflected wave each time, and then received at the receiving ultrasonic transducer, and
wherein the ultrasonic distance measure calculates propagation time of a first ultrasonic wave based on the intensity of a first received signal detected at the receiving section each time and measures a distance to the object of measurement based on the propagation time.

15. The ultrasonic distance measure of claim 14, wherein the time delay is fixed and the time interval is changed.

16. The ultrasonic distance measure of claim 14, wherein the time interval is fixed and the time delay is changed.

17. The ultrasonic distance measure of claim 16, wherein the receiving section locates the barycenter of the intensity of the first received signal on the axis of time delay and derives the propagating time of the first ultrasonic wave with respect to the barycenter.

18. The ultrasonic distance measure of claim 17, wherein the receiving control voltage generating section and the transmitting control voltage generating section generate the first control voltage that changes the resonant or resonance frequencies of the receiving and transmitting ultrasonic transducers substantially in sync with the frequency modulation of the first drive signal.

19. The ultrasonic distance measure of claim 18, wherein the driving section generates a second drive signal, which switches a first frequency into a second frequency, such that the measuring drive signal includes the second drive signal before the first drive signal, and wherein the receiving control voltage generating section generates a second control voltage, which produces resonance in the receiving ultrasonic transducer at the first frequency, before the first control voltage, and wherein the receiving ultrasonic transducer receives a second reflected wave resulting from a second ultrasonic wave that has been transmitted from the transmitting ultrasonic transducer toward the object of measurement in response to the second drive signal, and wherein the receiving section detects a variation in the intensity of a second received signal representing the second reflected wave, and sets the time delay based on results of detection.

20. An ultrasonic range finding method comprising the steps of:

transmitting an ultrasonic wave toward an object of measurement by driving a transmitting ultrasonic transducer with a frequency-modulated drive signal applied thereto and with its resonant or resonance frequency changed substantially in sync with the frequency modulation of the drive signal; and receiving the ultrasonic wave, which has been reflected from the object of measurement, at the receiving ultrasonic transducer with the resonant or resonance frequency thereof changed after a controllable amount of time delay has passed since the drive signal was generated, wherein the transmitting step and the receiving step are carried out a number of times with the time delay changed each time, and wherein the propagation time of the ultrasonic wave is obtained based on the time delay that makes the receiving ultrasonic transducer receive an ultrasonic wave with the highest signal intensity, and the distance to the object of measurement is calculated based on the propagation time.

* * * * *

UNITED STATES PATENT AND TRADEMARK OFFICE
CERTIFICATE OF CORRECTION

PATENT NO.        : 7,046,015 B2                                            Page 1 of 1
APPLICATION NO. : 11/214426
DATED             : May 16, 2006
INVENTOR(S)       : Takehiko Suginouchi, Koichi Saito and Masahiko Hashimoto It is certified that error appears in the above-identified patent and that said Letters Patent is hereby corrected as shown below:

Front Page, (Section 30), "Apr. 28, 2003" should read -- Apr. 28, 2004 --.

Front Page, Section (57), line 7, "The transducer" should read -- the transducer --; and line 13, "The drive signal" should read -- the drive signal --.

Signed and Sealed this

Thirteenth Day of March, 2007

JON W. DUDAS
*Director of the United States Patent and Trademark Office*